US011365441B2

(12) United States Patent
Dhingra et al.

(10) Patent No.: US 11,365,441 B2
(45) Date of Patent: Jun. 21, 2022

(54) METHOD AND APPARATUS FOR SIMULTANEOUS TARGETED SEQUENCING OF DNA, RNA AND PROTEIN

(71) Applicant: Mission Bio, Inc., South San Francisco, CA (US)

(72) Inventors: Dalia Dhingra, San Francisco, CA (US); Aik Ooi, San Mateo, CA (US); Pedro Mendez, San Mateo, CA (US); David Ruff, South San Francisco, CA (US)

(73) Assignee: Mission Bio, Inc., South San Francisco, CA (US)

( * ) Notice: Subject to any disclaimer, the term of this patent is extended or adjusted under 35 U.S.C. 154(b) by 74 days.

(21) Appl. No.: 16/882,289

(22) Filed: May 22, 2020

(65) Prior Publication Data
US 2020/0399686 A1 Dec. 24, 2020

Related U.S. Application Data

(60) Provisional application No. 62/904,374, filed on Sep. 23, 2019, provisional application No. 62/851,448, filed on May 22, 2019.

(51) Int. Cl.
*C12Q 1/6834* (2018.01)
*C12Q 1/6806* (2018.01)
*C12Q 1/686* (2018.01)

(52) U.S. Cl.
CPC ......... *C12Q 1/6834* (2013.01); *C12Q 1/6806* (2013.01); *C12Q 1/686* (2013.01); *C12Q 2521/107* (2013.01); *C12Q 2521/537* (2013.01)

(58) Field of Classification Search
CPC ............... C12Q 1/6834; C12Q 1/6806; C12Q 2521/107; C12Q 2521/537; C12N 15/1075
See application file for complete search history.

(56) References Cited

U.S. PATENT DOCUMENTS

| | | | |
|---|---|---|---|
| 7,638,276 B2 | 12/2009 | Griffiths et al. | |
| RE41,780 E | 9/2010 | Anderson et al. | |
| 8,067,159 B2 | 11/2011 | Brown et al. | |
| 8,257,925 B2 | 9/2012 | Brown et al. | |
| 8,765,485 B2 | 7/2014 | Link et al. | |
| 9,150,852 B2 | 10/2015 | Samuels et al. | |
| 10,161,007 B2 | 12/2018 | Abate et al. | |
| 10,501,739 B2 * | 12/2019 | Eastburn | C12Q 1/6869 |
| 2003/0156993 A1 | 8/2003 | Staats | |
| 2004/0253613 A1 | 12/2004 | Taylor et al. | |
| 2005/0019902 A1 | 1/2005 | Mathies et al. | |
| 2005/0112639 A1 | 5/2005 | Wang et al. | |
| 2007/0039866 A1 | 2/2007 | Schroeder et al. | |
| 2007/0077572 A1 | 4/2007 | Tawfik et al. | |
| 2007/0109530 A1 | 5/2007 | Ueno et al. | |
| 2007/0141593 A1 | 6/2007 | Lee et al. | |
| 2007/0206179 A1 | 9/2007 | Wang et al. | |
| 2007/0231880 A1 | 10/2007 | Chang-Yen et al. | |
| 2008/0014589 A1 | 1/2008 | Link et al. | |
| 2008/0274458 A1 | 11/2008 | Latham et al. | |
| 2009/0045064 A1 | 2/2009 | Simmons et al. | |
| 2009/0098555 A1 | 4/2009 | Roth et al. | |
| 2009/0122311 A1 | 5/2009 | Kanda | |
| 2009/0170715 A1 | 7/2009 | Glinsky | |
| 2010/0015614 A1 | 1/2010 | Beer et al. | |
| 2010/0028915 A1 | 2/2010 | Gualberto et al. | |
| 2010/0055677 A1 | 3/2010 | Colston, Jr. et al. | |
| 2010/0173394 A1 | 7/2010 | Colston, Jr. et al. | |
| 2010/0285975 A1 | 11/2010 | Mathies et al. | |
| 2011/0053798 A1 | 3/2011 | Hindson et al. | |
| 2011/0056575 A1 | 3/2011 | Hong et al. | |
| 2011/0059556 A1 * | 3/2011 | Strey | B01L 3/502761 436/518 |
| 2011/0103176 A1 | 5/2011 | Van Dam et al. | |
| 2011/0104816 A1 | 5/2011 | Pollack et al. | |

(Continued)

FOREIGN PATENT DOCUMENTS

AU   2013203624 A1   5/2013
AU   2013302867 A1   2/2015

(Continued)

OTHER PUBLICATIONS

Macaulay et al., Trends in Genetics, 33(2), 155-168, 02 (Year: 2017).*
Ali, et al., "Rolling Circle Amplification: a Versatile Tool for Chemical Biology, Materials Science and Medicine," Journal, Mar. 18, 2017, pp. 3324-3341, vol. 43, Chem Soc Rev.
Extended European Search Report received for European Patent Application Serial No. 15812857.9 dated Oct. 17, 2017, 7 pages.
Extended European Search Report received for European Patent Application Serial No. 15853268.9 dated Sep. 33, 2018, 12 pages.
Extended European Search Report received for European Patent Application Serial No. 16747224.0 dated May 24, 2018, 9 pages.
Extended European Search Report received for European Patent Application Serial No. 16747229.9 dated Sep. 10, 2018, 8 pages.

(Continued)

*Primary Examiner* — Cynthia B Wilder
(74) *Attorney, Agent, or Firm* — Goodwin Procter LLP

(57) ABSTRACT

Provided herein are methods and systems for the simultaneous targeted detection and sequencing of DNA, RNA, and Protein. In typical embodiments, the DNA, RNA, and Proteins are detected, characterized, and sequenced using just a single mammalian cell. One embodiment of detecting and characterizing DNA, RNA, or protein from a mammalian cell includes encapsulating a single cell in a drop and performing a protease digest on the encapsulated cell drop, performing a reverse transcriptase reaction; performing a droplet merger with barcoding PCR reagents and barcoding beads; performing a PCR reaction to attach the cell barcodes to the DNA targeted amplicons, RNA targeted amplicons, and protein tag amplicons, where all amplicons from the same emulsion contain the same cell barcode; and detecting and characterizing a DNA, RNA, or protein amplicon by sequencing the cell barcode incorporated into each amplicon.

18 Claims, 11 Drawing Sheets

(56) References Cited

U.S. PATENT DOCUMENTS

| | | |
|---|---|---|
| 2011/0118151 A1 | 5/2011 | Eshoo et al. |
| 2011/0160078 A1 | 6/2011 | Fodor et al. |
| 2011/0217736 A1 | 9/2011 | Hindson |
| 2011/0311978 A1 | 12/2011 | Makarewicz, Jr. et al. |
| 2012/0010086 A1 | 1/2012 | Froehlich et al. |
| 2012/0045765 A1 | 2/2012 | Curran et al. |
| 2012/0094848 A1 | 4/2012 | Rigatti et al. |
| 2012/0122714 A1 | 5/2012 | Samuels et al. |
| 2012/0170739 A1 | 7/2012 | Karroumi et al. |
| 2012/0190032 A1 | 7/2012 | Ness et al. |
| 2012/0190033 A1 | 7/2012 | Ness et al. |
| 2012/0196288 A1 | 8/2012 | Beer et al. |
| 2012/0219947 A1 | 8/2012 | Yurkovetsky et al. |
| 2012/0220494 A1 | 8/2012 | Samuels et al. |
| 2012/0258870 A1 | 10/2012 | Schwartz et al. |
| 2012/0264646 A1 | 10/2012 | Link et al. |
| 2012/0270306 A1 | 10/2012 | Vacca et al. |
| 2012/0309002 A1 | 12/2012 | Link |
| 2012/0316074 A1 | 12/2012 | Saxonov |
| 2013/0032235 A1 | 2/2013 | Johnstone et al. |
| 2013/0046030 A1 | 2/2013 | Rotem et al. |
| 2013/0084572 A1 | 4/2013 | Hindson et al. |
| 2013/0095469 A1 | 4/2013 | Koltay et al. |
| 2013/0116130 A1 | 5/2013 | Fu et al. |
| 2013/0130919 A1 | 5/2013 | Chen et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0224736 A1 | 8/2013 | Marie et al. |
| 2013/0236901 A1 | 9/2013 | Potier et al. |
| 2013/0295567 A1 | 11/2013 | Link et al. |
| 2013/0295587 A1 | 11/2013 | Sjobom |
| 2014/0057799 A1 | 2/2014 | Johnson et al. |
| 2014/0154695 A1 | 6/2014 | Miller et al. |
| 2014/0155295 A1 | 6/2014 | Hindson et al. |
| 2014/0179544 A1 | 6/2014 | Steenblock et al. |
| 2014/0186840 A1 | 7/2014 | Ding et al. |
| 2014/0199731 A1 | 7/2014 | Agresti et al. |
| 2014/0272988 A1 | 9/2014 | Zador et al. |
| 2014/0323316 A1 | 10/2014 | Drmanac et al. |
| 2014/0378345 A1 | 12/2014 | Hindson et al. |
| 2014/0378349 A1 | 12/2014 | Hindson et al. |
| 2015/0232942 A1 | 8/2015 | Abate et al. |
| 2015/0298091 A1 | 10/2015 | Weitz et al. |
| 2015/0322507 A1 | 11/2015 | Zimmermann et al. |
| 2015/0376609 A1 | 12/2015 | Hindson et al. |
| 2016/0061711 A1 | 3/2016 | Deka |
| 2016/0177375 A1 | 6/2016 | Abate et al. |
| 2017/0005665 A1 | 1/2017 | Swaminathan et al. |
| 2017/0009274 A1 | 1/2017 | Abate et al. |
| 2017/0009275 A1 | 1/2017 | Menchen et al. |
| 2017/0022538 A1 | 1/2017 | Abate et al. |
| 2017/0121756 A1 | 5/2017 | Abate et al. |
| 2017/0145508 A1 | 5/2017 | Koh et al. |
| 2017/0192013 A1 | 7/2017 | Agresti |
| 2017/0268056 A1 | 9/2017 | Vigneault et al. |
| 2017/0272956 A1 | 9/2017 | Gu et al. |
| 2018/0008112 A1 | 1/2018 | Ham et al. |
| 2018/0051277 A1 | 2/2018 | Godfrey et al. |
| 2018/0056288 A1 | 3/2018 | Abate et al. |
| 2018/0088112 A1 | 3/2018 | Sharma et al. |
| 2018/0208975 A1 | 7/2018 | Peterson et al. |
| 2018/0216160 A1 | 8/2018 | Abate et al. |
| 2018/0237836 A1 | 8/2018 | Abate et al. |
| 2018/0267036 A1 | 9/2018 | Fan |
| 2018/0284125 A1 | 10/2018 | Gordon et al. |
| 2018/0304222 A1 | 10/2018 | Weitz et al. |
| 2018/0346969 A1 | 12/2018 | Chang et al. |
| 2018/0355407 A1 | 12/2018 | Utharala et al. |
| 2019/0025304 A1 | 1/2019 | Vigneault et al. |
| 2019/0153513 A1 | 5/2019 | Dallett et al. |
| 2019/0169689 A1 | 6/2019 | Zhu et al. |
| 2019/0169700 A1 | 6/2019 | Abate et al. |
| 2019/0172582 A1 | 6/2019 | Onuchic et al. |
| 2019/0218594 A1 | 7/2019 | Abate et al. |
| 2019/0241965 A1 | 8/2019 | Abate et al. |
| 2019/0330701 A1 | 10/2019 | Abate et al. |
| 2019/0352708 A1 | 11/2019 | Gaige et al. |
| 2020/0087707 A1 | 3/2020 | Engreitz |
| 2020/0124601 A1 | 4/2020 | Fan et al. |
| 2020/0173992 A1 | 6/2020 | Fan et al. |
| 2020/0362334 A1 | 11/2020 | Regev et al. |
| 2021/0009994 A1 | 1/2021 | Godron et al. |

FOREIGN PATENT DOCUMENTS

| | | |
|---|---|---|
| AU | 2016215298 A1 | 8/2017 |
| AU | 2019226236 A1 | 9/2019 |
| CA | 2881783 A1 | 2/2014 |
| CA | 3001986 A1 | 4/2016 |
| CA | 2974299 A1 | 8/2016 |
| CA | 2974306 A1 | 8/2016 |
| CN | 1693478 A | 11/2005 |
| CN | 104736725 A | 6/2015 |
| CN | 107107058 A | 8/2017 |
| CN | 107429426 A | 12/2017 |
| CN | 107530654 A | 1/2018 |
| CN | 108350488 A | 7/2018 |
| CN | 110088290 A | 8/2019 |
| DE | 10339452 A1 | 3/2005 |
| EP | 1547677 A1 | 6/2005 |
| EP | 2145955 A2 | 1/2010 |
| EP | 2565650 A1 | 3/2013 |
| EP | 2882872 A2 | 6/2015 |
| EP | 3160654 A2 | 5/2017 |
| EP | 3209419 A1 | 8/2017 |
| EP | 3253479 A2 | 12/2017 |
| EP | 3253910 A1 | 12/2017 |
| EP | 3337907 A1 | 6/2018 |
| EP | 3497228 A1 | 6/2019 |
| GB | 2519906 A | 5/2015 |
| GB | 2539836 B | 3/2017 |
| JP | 2013503630 A | 2/2013 |
| JP | 2015533079 A | 11/2015 |
| JP | 2018505671 A | 3/2018 |
| JP | 2018508198 A | 3/2018 |
| JP | 2018525004 A | 9/2018 |
| WO | 9412216 A1 | 6/1994 |
| WO | 2007140015 A2 | 12/2007 |
| WO | 2009050512 A2 | 4/2009 |
| WO | 2009054870 A2 | 4/2009 |
| WO | 2009111014 A2 | 9/2009 |
| WO | 2010148039 A2 | 12/2010 |
| WO | 2011047307 A1 | 4/2011 |
| WO | 2012011091 A2 | 1/2012 |
| WO | 2012048341 A1 | 4/2012 |
| WO | 2012083225 A2 | 6/2012 |
| WO | 2012109600 A2 | 8/2012 |
| WO | 2012142213 A2 | 10/2012 |
| WO | 2012156744 A3 | 11/2012 |
| WO | 2012162267 A2 | 11/2012 |
| WO | 2013119753 A1 | 8/2013 |
| WO | 2013126741 A1 | 8/2013 |
| WO | 2013130512 A2 | 9/2013 |
| WO | 2013134261 A1 | 9/2013 |
| WO | 2013173394 A2 | 11/2013 |
| WO | 2014028378 A2 | 2/2014 |
| WO | 2014028537 A1 | 2/2014 |
| WO | 2014047556 A2 | 3/2014 |
| WO | 2014083435 A2 | 6/2014 |
| WO | 2014093676 A1 | 6/2014 |
| WO | 2014108323 A1 | 7/2014 |
| WO | 2014138132 A2 | 9/2014 |
| WO | 2014151658 A1 | 9/2014 |
| WO | 2014153071 A1 | 9/2014 |
| WO | 2015031691 A1 | 3/2015 |
| WO | 2015069798 A1 | 5/2015 |
| WO | 2015120398 A1 | 8/2015 |
| WO | 2015157369 A1 | 10/2015 |
| WO | 2015189336 A1 | 12/2015 |
| WO | 2015200717 A2 | 12/2015 |
| WO | 2016064755 A2 | 4/2016 |
| WO | 2016065056 A1 | 4/2016 |
| WO | 2016126865 A1 | 8/2016 |

(56) References Cited

FOREIGN PATENT DOCUMENTS

| WO | 2016126871 A2 | 8/2016 |
|---|---|---|
| WO | 2015164212 A9 | 10/2016 |
| WO | 2017/004153 A1 | 1/2017 |
| WO | 2017031125 A1 | 2/2017 |
| WO | 2017218486 A1 | 12/2017 |
| WO | 2018/022581 A1 | 2/2018 |
| WO | 2018119301 A1 | 6/2018 |
| WO | 2018/144813 A1 | 8/2018 |
| WO | 2018/226293 A1 | 12/2018 |
| WO | WO-2019/023263 A1 | 1/2019 |
| WO | 2019/079640 A1 | 4/2019 |
| WO | WO-2020/206184 A1 | 10/2020 |

OTHER PUBLICATIONS

Extended European Search Report received for European Patent Application Serial No. 16837703.4 dated Nov. 29, 2018, 9 pages.

Fu, Yusi et al (2015) "Uniform and accurate single-cell sequencing based on emulsion whole-genome amplification"; Proc Natl Acad Sci US A. 112(38); pp. 11923-11928.

Grover, et al. "Multiple Displacement Amplification as a pre-Polymerase Chain Reaction (pre-PCR) to Detect Ultra Low Population of Ralstonia Solanacearum (Smith 1896) Yabuchi et al. (1996)" Journal, 2009, pp. 539-543, 49(5), Lett Appl Microbiol.

International Preliminary Report on Patentability received for PCT Application Serial No. PCT/US2017/037175 dated Dec. 18, 2018, 3 pages.

International Search Report and Written Opinion for PCT/US20/14595, dated Apr. 29, 2020.

International Search Report and Written Opinion received for PCT Application Serial No. PCT/US2013/054517 dated Feb. 21, 2014, 18 pages.

International Search Report and Written Opinion received for PCT Application Serial No. PCT/US2015/037822 dated Feb. 2, 2016, 9 pages.

International Search Report and Written Opinion received for PCT Application Serial No. PCT/US2015/56743 dated Mar. 3, 2016, 12 pages.

International Search Report and Written Opinion received for PCT Application Serial No. PCT/US2016/016438 dated Jun. 10, 2016, 14 pages.

International Search Report and Written Opinion received for PCT Application Serial No. PCT/US2016/016444 dated Jul. 27, 2016, 43 pages.

International Search Report and Written Opinion received for PCT Application Serial No. PCT/US2016/47199 dated Dec. 12, 2016, 10 pages.

International Search Report and Written Opinion received for PCT Application Serial No. PCT/US2017/046159 dated Nov. 21, 2017, 12 pages.

International Search Report and Written Opinion received for PCT Application Serial No. PCT/US2017/068006 dated Mar. 26, 2018, 9 pages.

International Search Report and Written Opinion to PCT Application No. PCT/US18/57410 dated Feb. 8, 2019.

International Search Report received for PCT Application Serial No. PCT/US2017/037175 dated Aug. 28, 2017, 3 pages.

Lan, et al., "Single-Cell Genome Sequencing at Ultra-High-Throughput with Microfluidic Droplet Barcoding," journal, Jul. 2017, pp. 640-646, vol. 35, No. 7, Nature Biotechnology.

Nishikawa, Yohei et al (2015) "Monodisperse Picoliter Droplets for Low-Bias and Contamination-Free Reactions in Single-Cell Whole Genome Amplification" PLoS One 10(9); pp. e0138733.

Pellegrino, et al., "High-Throughput Single-Cell DNA sequencing of AML Tumors with Droplet Microfluidics," bioRxiv preprint posted online, Oct. 13, 2017, 21 pages, http://dx.doi.org/10.1101/203158.

Sciambi et al. (2013) "Adding reagent to droplets with controlled rupture of encapsulated double emulsions"; Biomicrofluidics 7(4); pp. 1-6.

Sidore, et al (2016) "Enhanced sequencing coverage with digital droplet multiple displacement amplification"; Nuclei. Acids Res. 44(7):e66.; pp. 1-9.

Written Opinion received for PCT Application Serial No. PCT/US2017/037175 dated Aug. 28, 2017, 4 pages.

Yu, et al (2014) "Mung bean nuclease treatment increases capture specificity of microdroplet-PCR based targeted DNA enrichment"; PLoS One 9(7):e103491; pp. 1-7.

Zeng, et al., "High Performance Single Cell Genetic Analysis Using Microfludic Emulsion Generator Arrays," journal, Apr. 15, 2010, pp. 3138-3190, vol. 82, No. 8, Analytical Chemistry.

Zhu, et al., "Highly Sensitive and Quantitative Detection of Rare Pathogens Through Agarose Droplet Microfluidic Emulsion PCR at the Single-Cell Level," Journal, 2012, pp. 3907-3913, 12(20), Lab on a Chip.

Abate, et al., "Efficient Encapsulation With Plug-Triggered Drop Formation," Journal, 2011, 84(3):031502, Physical Review E.

Abate, et al., "Faster Multiple Emulsification with Drop Splitting," Journal 2011, pp. 1911-1915, 11(11), Lab on a Chip.

Abate, et al., "High-Throughput Injection With Microfluidics Using Picoinjectors," Journal, Nov. 9, 2010, pp. 19163-19166, vol. 107 1 No. 45, PNAS.

Abate, et al., "Microfluidic Sorting With High-Speed Single-Layer Membrane Valves," Journal, 2010, pp. 203509-1-203509-3, Applied Physics Letters 96.

Abate, et al., "One-Step Formation of Multiple Emulsions in Microfluidics," Journal, 2011, pp. 253-258, 11(2), Lab on a Chip.

Abate, et al., "Photoreactive Coating for High-Contrast Spatial Patterning of Microfluidic Device Wettability," Journal, 2008, pp. 2157-2160, 8(12), Lab on a Chip.

Agresti, et al., "Correction for Ultrahigh-throughput Screening in Drop-Based Microfluidics for Directed Evolution," Journal, 2010, pp. 6550-6551, 107, Proc. Natl Acad Sci., US.

Agresti, et al., "Ultrahigh-Throughput Screening in Drop-Based Microfluidics for Firected Evolution," Journal, 2008, pp. 4004-4009, vol. 107, No. 9, PNAS.

Ahn, et al., "Electrocoalescence of Drops Synchronized by Size-Dependent Flow in Microfluidic Channels," Journal, 2006, pp. 264105-1-264105-3, Appl Phys Lett 88.

Allen, et al., "Single Virus Genomics: A New Tool for Virus Discovery," Journal, 2011, 6(3):e17722, PLoS One.

Arriaga, et al. "Ultrathin Shell Double Emulsion Templated Giant Unilamellar Lipid Vesicles With Controlled Microdomain Formations," Journal, 2014, pp. 950-956, 10(5), Small.

Atten, "Electrocoalescence of Water Droplets in an Insulating Liquid" Journal, 1993, pp. 259-569, J Electrostat 30.

AU Examination Report dated Oct. 3, 2018, to AU Patent Application No. 2013302867.

Barenholz, et al. "A Simple Method for the Preparation of Homogeneous Phospholipid Vesicles" Journal, 1977, pp. 2806-2810, 12(12), Biochemistry.

Battaglia, et al. "Polymeric Vesicle Permeability: A Facile Chemical Assay" Journal, 2006, pp. 4910-4913, 22(11), Langmuir.

Beer, et al. "On-Chip Single-Copy Real-0Time Reverse-Transcription PCR in Isolated Picoliter Droplets" Journal, 2008, pp. 1854-1858, Anal Chem 80.

Bird, et al. "Single-Chain Antigen-Binding Proteins" Journal, 1988, pp. 423-426, Science 242.

Blainey PC "The Future is Now: Single-Cell Genomics of Bacteria and Archaea" Journal, 2013, pp. 407-427, 37(3), FEMS Microbiology Reviews.

Brouzes, et al., "Droplet Microfluidic Technology for Single-Cell High-Throughput Screening," Journal, Aug. 25, 2009, pp. 14195-14200, vol. 106 No. 34, PNAS.

Brown, et al, "Current Techniques for Single-Cell Lysis" Journal, 2008, pp. S131-S138, J.R. Soc. Interface 5.

Caron, "Assessment of Bacterial Viabiligy Status by Flow Cytometry and Single Cell Sorting," Journal, 1998, pp. 988-998, 84(6), Journal of Applied Microbiology.

(56) References Cited

OTHER PUBLICATIONS

Chabert, et al. "Droplet Fusion by Alternating Current (AC) Field Electrocoalesence in Microchannels" Journal, 2005 pp. 3706-3715, Electrophoresis 26.
Chaffer, et al., "A Perspective on Cancer Cell Metastasis" Journal, Mar. 25, 2011, pp. 1559-1564, vol. 331, Science.
Chen, et al. "Influence of pH on the Stability of Oil-In-Water Emulsions Stabilized by a Splittable Surfactant," Journal, 2000, pp. 173-179, 170(2), Colloids and Surfaces A: Physicochemical and Engineering Aspects.
Chung, et al., "Droplet Dynamics Passing Through Obstructions in Confined Microchannel Flow," Journal, 2010, pp. 1151-1163, 9(6), Microfluidics Nanofluidics.
Clausell-Tormos, et al., "Droplet-Based Microfluidic Platforms for the Encapsulation and Screening of Mammalian Cells and Multicellular Organismsm" Journal, May 2008, pp. 427-437, Chemistry and Biology 15.
Dejournette CJ, et al; (2013) "Creating Biocompatible Oil-Water Interfaces without Synthesis: Direct Interactions between Primary Amines and Carboxylated Perfluorocarbon Surfactants"; Analytical chemistry.;85(21); pp. 10556-10564.
Dietrich et al; "Effects of UV irradiation and hydrogen peroxide on DNA fragmentation, motility and fertilizing ability of rainbow trout (*Oncorhynchus mykiss*) spermatozoa"; Theriogenology. vol. 64; (Nov. 2005) pp. 1809-1822.
Duffy DC, et al; (1998) "Rapid Prototyping ofMicrofluidic Systems in Poly(dimethylsiloxane)"; Anal. Chem. 70; pp. 4974-4984.
Eastburn Dennis J., et al; (2013) "Ultrahigh-Throughput Mammalian Single-Cell Reverse-Transcriptase Polymerase Chain Reaction in Microfluidic Drops"; Anal. Chem. 85; pp. 8016-8021.
Eastburn DJ,et al; (2013) "Picoinjection Enables Digital Detection of RNA with Droplet RT-PCR"; PloS one.;8(4): e62961.
Edd et al., (2008) Controlled encapsulation of single cells into monodisperse picoliter drop Lab on a Chip, 8(8); pp. 1262-1264.
emPCR-amplification manual for GS-FLX series (May 2011); 454 Life Science Corp; 12 pages.
Extended EP Search Report dated Feb. 8, 2016, to EP Patent Application No. 13829925.0.
Final Office Action dated Oct. 18, 2019, to U.S. Appl. No. 16/164,595.
First Action Interview—Office Action dated Sep. 7, 2016, to U.S. Appl. No. 15/047,555.
First Office action received for Chinese Patent Application Serial No. 2013800532581 dated Feb. 22, 2016, 2 pages.
First Office action received for Chinese Patent Application Serial No. 2015800704110 dated Dec. 13, 2018, 2 pages.
Frenz L, et al; (2009) "Reliable microfluidicon-chip incubation of droplets in delay-lines"; Lab on a Chip 9(10); pp. 1344-1348.
Garstecki P. et al; "Formation of droplets and bubbles in a microfluidic T-junction-scaling and mechanism of break-up"; Lab Chip 6; (2006); pp. 437-446.
Gevensleben H, et al; (2013) "Noninvasive Detection ofHER2 Amplification with Plasma DNA Digital PCR"; Clinical Cancer Research.; 19(12); pp. 3276-3284.
Gribskov, et al; (1986) "Sigma factors from *E. coli, B. subtilis*, phage SP01, and phage T4 are homologous proteins"; Nucl. Acids Res. 14(6):6745-6763.
Hayward RC, et al; (2006) "Dewetting instability during the formation of polymersomes from block-copolymer-stabilized double emulsions"; Langmuir 22(10); pp. 4457-4461.
Herminghaus S, "Dynamical Instability of Thin Liquid Films Between Conducting Media"; Physical Review Letter, vol. 83, No. 12; Sep. 20, 1999; pp. 2359-2361.
Holland, et al; (1991) "Detection of specific polymerase chain reaction product by utilizing the 5'-3' exonuclease activity ofThermus aquaticus DNA polymerase"; PNAS, 88 (16); 7276-7280.
Holtyze C., et al; (2008) "Biocompatible surfactants for water-in-fluorocarbon emulsions"; Lab Chip 8; pp. 1632-1639.
Horton et al; "Gene splicing by overlap extension: tailor-made genes using the polymerase chain reaction"; Biotechniques, vol. 54; Mar. 1, 2013; pp. 129-133.

Hu, Hoa et al; (2009) "Mutation screening in 86 known X-linked mental retardation genes by droplet-based multiplex PCR and massive parallel sequencing"; Hugo J.3; pp. 41-49.
Huebner, et al; (2008) "Microdroplets: A sea of applications?"; Lab on a Chip, 8; pp. 1244-1254.
Hunkapiller and Hood, (1986) "Immunology: The Growing Immunoglobulin Gene Superfamily"; Nature, 323; pp. 15-16.
Eastburn, et al., "Microfluidic Droplet Enrichment for Targeted Sequencing," journal, Apr. 14, 2015, pp. 1-8, vol. 43, Nucleic Acids Research.
European search report and opinion dated Feb. 8, 2016 for EP Application No. 13829925.
International Search Report and Written Opinion received for International Application No. PCT/US2018/056575, dated Jan. 3, 2019, 15 pages.
Kawasaki, "Sample Preparation From Blood, Cells, and Other Fluids," Book, 1990, Chapter 18 pp. 146-152, PCR Protocols: A Guide to Methods and Applications.
Kuster, et al., "Interfacing Droplet Microfluidics with Matrix-Assisted Laser Desorption/Ionization Mass Spectrometry: Label-Free Content Analysis of Single Droplets," Analytical Chemistry, 2013, pp. 1285-1289, 85, ACS Publications.
Lim, Shuan and Abate Adam, (2013) "Ultrahigh-throughput sorting of microfluidic drops with flow cytometry"; Lab Chip13; pp. 4563-4572.
Medkov A, Martina et al; "Analyzing Cancer at Single Cell Resolution with Droplet Technology"; American Association of Cancer Research (AACR); Apr. 19, 2010; 1 page.
Scotts. H, et al; (2011) "Microfluidic immunomagnetic multi-target sorting—a model for controlling deflection of paramagnetic beads"; Lab Chip 11; pp. 2577-2582.
Sukovich, et al., "Bulk Double Emulsification for Flow Cytometric Analysis of Microfluidic Froplets," journal, Nov. 13, 2017, 5 pages, DOI:10.1039/c7an01695f, Royal Society of Chemistry.
Ullal, et al; (2014) "Cancer cell profiling by barcoding allows multiplexed protein analysis in fine needle aspirates"; Sci Transl Med. 6(219):219ra9; pp. 1-22.
Utada, et al; (2007) "Dripping to jetting transitions in co flowing liquid streams"; Phys Rev Lett. Aug. 31, 2007;99(9; pp. 094502-1-094502-4.
Vanapalli SA,et al; "Hydrodynamic resistance of single confined moving drops in rectangular microchannels"; Lab Chip 9 (2009); pp. 982-990.
Vickers, et al., (2006) "Generation of Hydrophilic Poly(dimethylsiloxane) for High-Performance Microchip Electrophoresis"; Anal. Chem, 78(21); pp. 7446-7452.
Wang C, et al; (2012) "Amphiphilic building blocks for self-assembly: from amphiphiles to supra-amphiphiles"; Accounts of Chemical Research 45(4); pp. 608-618.
Wheeler et al, (2005) "Digital microfluidics with in-line sample purification for proteomics analyses with MALDI-MS"; Anal Chem. 77(2); 534-540.
Whitcombe D, et al; (1999) "Detection of PCR products using self-probing amplicons and fluorescence"; Nature biotechnology 17(8); pp. 804-807.
Whitesides GM. (2006) The origins and the future ofmicrofluidics. Nature 442(7101); pp. 368-373.
Xia YN, et al; (1998) "Soft lithography"; Angew Chem Int Edit 37; pp. 551-575.
Zheng, B, et al; (2004) "Formation of droplets of in microfluidic channels alternating composition and applications to indexing of concentrations in droplet-based assays"; Anal Chem 76; pp. 4977-4982.
Zhong Qun, et al; (2011) "Multiplex digital PCR: breaking the one target per color barrier of quantitative PCR"; Lab Chip 11; pp. 2167-2174.
Zhu et al., (2001) "Reverse transcriptase template switching: a SMART approach for full-length cDNA library construction"; BioTechniques 30: pp. 892-897.
Zien TF; (1969) "Hydrodynamics of bolus flow—an analytical approach to blood flow in capillaries"; Math Biophys, 31; pp. 681-694.

(56) References Cited

OTHER PUBLICATIONS

Hunt JA, et al; (1994) "Effect of pH on the stability and surface composition of emulsions made with whey protein isolate"; Journal of Agricultural and Food Chemistry.;42(10); pp. 2131-2135.
Huston et al; (1988) "Protein engineering of antibody binding sites: recovery of specific activity in an anti-digoxin single-chain Fv analogue produced in *Escherichia coli*"; Proc. Nal Acad. Sci. U.S.A., 85; pp. 5879-5883.
International Search Report and Written Opinion received for International Application No. PCT/US2018/057410, dated Feb. 8, 2019, 14 pages.
Kiss MM, et al.(2008) "High-Throughput Quantitative Polymerase Chain Reaction in Picoliter Droplets"; Anal Chem 80(23); pp. 8975-8981.
Kritikou Ekat; "It's cheaper in the Picolab"; Nat Rev Genet, 6; (Sep. 2005); pp. 668.
Lagally ET, et al; (2001) "Single-Molecule DNA Amplification and Analysis in an Integrated Microfluidic Device"; Analytical Chemistry.;73(3); pp. 565-570.
Lanza Vecchia et al; (1987) "The use of hybrid hybridomas to target human cytotoxic T lymphocytes"; Eur. J. Immunol. 17(1); pp. 105-111.
Leary JF. (1994) "Strategies for rare cell detection and isolation"; Methods Cell Biol.;42(Pt B); pp. 331-358.
Link, et al; (2004) "Geometrically mediated breaknp of drops in microfluidic devices"; Phys Rev Lett. 92(5):054503.
Livak KJ and Schmittgen TD; (2001) "Analysis of Relative Gene Expression Data Using Real-Time Quantitative PCR and the 2<sup>-ΔΔCT</sup> Method"; methods.;25(4); pp. 402-408.
Longo MC, et al; (1990) "Use of uracil DNA glycosylase to control carry-over contamination in polymerase chain reactions"; Gene.;93(1); pp. 125-128.
Malloggi F, et al; "Electrowetting-controlled droplet generation in a microfluidic flow-focusing device"; J. Phys.: Condens. Matter 19; (2007); 462101; 7 pages.
Marcus et al., "Parallel Picoliter RT-PCR Assays Using Microfluidics"; Analytical Chemistry, 78(3); (2006); pp. 956-958.
Markou Athina,et al; (2011) "Molecular Characterization of Circulating Tumor Cells in Breast Cancer by a Liquid Bead Array Hybridization Assay"; Clinical Chemistry 57:3; pp. 421-430.
Mary P Pascaline, et al; "Controlling droplet incubation using close-packed plug flow"; Biomicrojluidics 5; (2011); pp. 024101-1-024101-6.
Mazutis L, et al; (2013) "Single-cell analysis and sorting using droplet-based microfluidics"; Nature protocols.8(5); pp. 870-891.
McDonald, et al; (2000) "Fabrication of microfluidic systems in poly( dimethylsiloxane"; Electrophoresis, 21 (I); pp. 27-40.
Metzker, Michael L. "Sequencing technologies—the next generation"; Nature Reviews Genetics, vol. 11 (Jan. 2010); pp. 31-46.
Miyazaki et al. (2013) "A new large-DNA-fragment delivery system based on integrase activity from an integrative and conjugative element"; Appl Environ Microbiol 79(14); pp. 4440-4447.
Miyazaki, K; (2002) "Random DNA fragmentation with endonuclease V: application to DNA shuffling"; Nucleic Acids Res. 30(24); e139.
Moon Sangjun, et al; "Drop-on-Demand Single Cell Isolation and Total RNA Analysis"; PloS ONE, vol. 6, Issue 3; e17455 (Mar. 2011); pp. 1-10.
Morton et al; (2008) "Crossing microfluidic streamlines to lyse, label and wash cellst"; Lab on a Chip, 8(9); pp. 1448-1453.
Mui B, et al; (1993) "Osmotic properties oflarge unilamellar vesicles prepared by extrusion"; Biophysical journal 64(2); pp. 443-453.
Nagrath Sunitha, et al; "Isolation of rare circulating tumour cells in cancer patients by microchip technology"; Nature 450(7173); Dec. 20, 2007; pp. 1235-1239.
Nakano M, et al. (2005) "Single-molecule reverse transcription polymerase chain reaction using water-in-oil emulsion"; J Biosci Bioeng 99; pp. 293-295.
Nikolova AN and Jones MN; (1996) "Effect of grafted PEG-2000 on the size and permeability of vesicles"; Biochimica et Biophysica Ada (BBA)—Lipids and Lipid Metabolism.; 1304(2); pp. 120-128.

Oberholzer,Thomas, et al; (1995) "Polymerase chain reaction in liposomes"; Chemistry & Biology vol. 2 No. 10; pp. 677-682.
O'Donovan B, et al; (2012) "Electrode-free picoinjection of microfluidic drops"; Lab Chip 12; pp. 4029-4032.
Okochi M et al; (2010) "Droplet-based gene expression analysis using a device with magnetic force-based-droplet-handling system"; J Biosci Bioeng. 109(2); pp. 193-197.
Perry DJ; (1999) "Solid-Phase Sequencing of Biotinylated PCR Products with Streptavidin-Coated Magnetic Beads"; Hemostasis and Thrombosis Protocols: Springer;. p. 49-54.
Piatek AS, et al; (1998) "Molecular beacon sequence analysis for detecting drug resistance in *Mycobacterium tuberculosis*";. Nat Biotechnol. 16(4); pp. 359-363.
Priest Craig, et al; (2006) "Controlled electrocoalescence in microfluidics: Targeting a single lamella"; Appl Phys Lett, 89; pp. 134101-1-134101-3.
Sciambia Adam and Abate Adam R., (2015) "Accurate microfluidic sorting of droplets at 30 kHz"; Lab Chip 15(1); pp. 47-51.
Seemann R, et al; (2012) "Droplet based microfluidics"; Rep Prag Phys 75; pp. 016601.
Shui et al; (2011) "Microfluidic DNA fragmentation for on-chip genomic analysis" Nanotechnology 22(49): 494013. 7 pages.
Siegel Adam C,et al; (2007) "Microsolidics: Fabrication of Three-Dimensional Metallic Microstructures in Poly ( dimethylsiloxane )"; Adv Mater 19; pp. 727-733.
Song H, et al; (2006) "Reactions in droplets in microfluidic charmels" Angew Chem Int Ed Engl 45; pp. 7336-7356.
Squires Tom M.; "Microfluidics: Fluid physics at the nanoliter scale"; Reviews of modem physics.;77(3); (Jul. 2005) pp. 977-1026.
Stone HA, et al; (2004) "Engineering flows in small devices: microfluidics toward a lab-on-a-chip"; Annu Rev Fluid Mech.;36; pp. 381-411.
Stott Shannon L; et al; "Isolation of circulating tumor cells using a microvortex-generating herringbone-chip"; PNAS vol. 107, No. 43; Oct. 26, 2010; pp. 18392-18397.
Syed et al. (2009) "Next-generation sequencing library preparation: simultaneous fragmentation and tagging using in vitro transposition"; Nature Methods vol. 6; pp. 1-2.
Tadmor AD, et al; (2011) "Probing individual enviromnental bacteria for viruses by using microfluidic digital PCR"; Science.;333(6038); pp. 58-62.
Takagi et al. (2005) "Continuous particle separation in a microchannel having asymmetrically arranged multiple branches" Lab Chip, 5(7); pp. 778-784.
Tamminen, et al. "Single Gene-Based Distinction of Individual Microbial Genomes from a Mixed Population of Microbial Cells," Journal, 2015, pp. 1-10, 6:195, Front Microbiol.
Teh SY,et al; "Droplet microfluidics"; Lab Chip 8; (2008); pp. 198-220.
Tewhey Ryan, et al; "Microdroplet-based PCR enrichment for large-scale targeted sequencing"; Nature Biotechnology, vol. 27 No. II; (Nov. 2009); pp. 1025-1035.
Thomann Y, et al; (2005) "PMMA Gradient Materials and in situ Nanocoating via Self-Assembly ofSemifluorinated Hyperbranched Amphiphiles"; Macromolecular Chemistry and Physics.;206(1); pp. 135-141.
Thorsen T, et al; (2001) "Dynamic pattern formation in a vesicle-generating microfluidic device"; Phys Rev Lett 86; pp. 4163-4166.
Tsai Scott S. H., et al; (2011) "Microfluidic immunomagnetic multi-target sorting—a model for controlling deflection of paramagnetic beads"; Lab Chip 11; pp. 2577-2582.
International Preliminary Report on Patentability issued to PCT Application No. PCT/US2018/046762 dated Feb. 18, 2020.
International Preliminary Report on Patentability received for PCT Application Serial No. PCT/US2013/054517 dated Feb. 26, 2015, 14 pages.
International Preliminary Report on Patentability received for PCT Application Serial No. PCT/US2015/037822 dated Jan. 5, 2017, 7 pages.
International Preliminary Report on Patentability received for PCT Application Serial No. PCT/US2015/56743 dated May 4, 2017, 9 pages.

(56) References Cited

OTHER PUBLICATIONS

International Preliminary Report on Patentability received for PCT Application Serial No. PCT/US2016/016438 dated Aug. 17, 2017, 10 pages.
International Preliminary Report on Patentability received for PCT Application Serial No. PCT/US2016/016444 dated Aug. 17, 2017, 40 pages.
International Preliminary Report on Patentability received for PCT Application Serial No. PCT/US2016/47199 dated Mar. 1, 2018, 8 pages.
International Preliminary Report on Patentability received for PCT Application Serial No. PCT/US2017/046159 dated Feb. 21, 2019, 9 pages.
International Preliminary Report on Patentability received for PCT Application Serial No. PCT/US2017/068006 dated Jul. 4, 2019, 7 pages.
International Search Report and Written Opinion dated Jun. 4, 2020, to PCT Application No. PCT/US2020/014488.
Non-Final Office Action dated Apr. 18, 2019, to U.S. Appl. No. 16/164,595.
Notice of Reasons for Rejection dated Dec. 19, 2019, to JP Patent Application No. 2017-539228.
Baret, et al. "Fluorescence-activated Droplet Sorting (FADS): Efficient Microfluidic Cell Sorting Based on Enzymatic Activitys," Journal, 2009, pp. 1850-1858, 9(13), Lab on a Chip.
Bernath, et al., "In Vitro Compartmentalization by Double Emulsions: Sorting and Gene Enrichment by Fluorescence Activated Cell Sorting" Journal, 2004, pp. 151-157, Analytical Biochemistry 325.
Final Office Action dated Apr. 18, 2018, to U.S. Appl. No. 15/047,555.
Final Office action dated Apr. 2, 2018, to U.S. Appl. No. 14/420,646.
Final Office Action dated Apr. 28, 2020, to U.S. Appl. No. 15/015,015.
Final Office Action dated Dec. 11, 2018, to U.S. Appl. No. 15/014,976.
Final office action dated Jan. 27, 2020, to U.S. Appl. No. 16/382,080.
Final Office Action dated Jun. 22, 2018, to U.S. Appl. No. 15/015,015.
Final Office action dated Sep. 21, 2018, to U.S. Appl. No. 15/317,393.
Ki, JS., et al. (2005) "Integrated method for single-cell DNA extraction, PCR amplification, and sequencing of ribosomal DNA from harmful Dinoflagellates Cochlodium polykrikoides and Alexandrium catenella"; Marine Biotechnology, vol. 6; pp. 587-593.
Non-Final office action dated Aug. 19, 2019, to U.S. Appl. No. 16/382,080.
Non-Final Office action dated Dec. 20, 2017, to U.S. Appl. No. 15/317,393.
Non-Final Office Action dated Jul. 12, 2017, to U.S. Appl. No. 15/015,015.
Non-Final Office action dated Jul. 14, 2017, to U.S. Appl. No. 14/420,646.
Non-Final office action dated Mar. 6, 2020, to U.S. Appl. No. 16/658,991.
Non-Final Office Action dated Mar. 8, 2018, to U.S. Appl. No. 15/014,976.
Non-Final Office Action dated Nov. 13, 2017, to U.S. Appl. No. 15/015,015.
Non-Final Office Action dated Oct. 10, 2019, to U.S. Appl. No. 15/014,976.
Novak, et al; (2011) "Single-cell multiplex gene detection and sequencing with microfluidically generated agarose emulsions"; Angew Chem Int Ed Engl. 50(2):390-395.
Nunes, et al. "Dripping and Jelling in Microfluidic Multiphase Flows Applied to Particle and Fiber Synthesis," Journal, 2013, 46(11), J Phys D Appl Phys, pii 114002.
Rolando, et al. "Cell Host & Microbe," 2013, pp. 395-405, 13.4.
Demaree et al., "Abstract 3527: Combined High-Throughput DNA Genotyping and Protein Quantification in Single Cancer Cells," Cancer Research, Jul. 1, 2019, vol. 79, Iss. 13, Suppl, pp. 1-1.
Kim et al., "Single-Cell RT-PCR in Microfluidic Droplets with Integrated Chemical Lysis," Anal Chem. 2018, vol. 90 No. 2, pp. 1273-1279.
Li et al., "Abstract 4696: High-Throughput Single-Cell Targeted DNA Sequencing Using an Updated Tapstri TM Platform Reveals Rare Clones and Clonal Evoluation for Multiple Blood Cancers," Cancer Research, Jul. 31, 2019, vol. 79, No. 13, Supplement, pp. 1-1.
Macaulay et al., "Single-Cell Multiomics: Multiple Measurements from Single Cells," Trends Genet, Feb. 2017, vol. 33(2), pp. 155-168.
Matuta et al., "Single-Cell Analysis Using Droplet Microfluidics," Adv Biosyst., 2020, vol. 4, Issue 1, pp. 1900188, Epub Nov. 26, 2019, PDF File: pp. 1-28.
McMahon et al., "Clonal Selection with RAS Pathway Activation Mediates Secondary Clinical Resistance to Selective FLT3 Inhibition in Acute Myeloid Leukemia," Cancer Discovery, vol. 9, pp. 1050-1063, May 14, 2019.
Notification of Transmittal of the International Search Report and the Written Opinion of the International Searching Authority, or the Declaration dated Feb. 10, 2021, Application No. PCT/US2020/054314, 16 pages.
PCT International Search Report and Written Opinion, App. No. PCT/US2020/026479, dated Jul. 23, 2020.
PCT International Search Report and Written Opinion, App. No. PCT/US2020/045949, dated Dec. 3, 2020.
PCT International Search Report and Written Opinion, App. No. PCT/US20/34404, dated Oct. 26, 2020.
PCT International Search Report and Written Opinion, App. No. PCT/US2020/026482, dated Aug. 3, 2020.
Shahi et al., "Abseq: Ultrahigh-throughput single cell protein profiling with droplet microfluidic barcoding," Scientific Reports, Mar. 14, 2017, vol. 7, No. 44447, pp. 1-12.
Whitesides, "The Origins and the Future of Microfluidics," Nature, vol. 442, No. 7101, pp. 368-373, 2006.
International Search Report, International Application No. PCT/US2020/026480, dated Jun. 25, 2020, 3 pages.

* cited by examiner

METHOD AND APPARATUS FOR SIMULTANEOUS TARGETED SEQUENCING OF DNA, RNA AND PROTEIN

RELATED APPLICATIONS

This application takes priority to the following U.S. Provisional Application U.S. Ser. No. 62/851,448 filed May 22, 2019 by D. Dhingra et al., and entitled 'Method and Apparatus For Simultaneous Targeted Sequencing Of DNA, RNA And Protein'; and U.S.S.N., all incorporated by reference herein.

FIELD

This invention relates generally to methods and systems for the simultaneous targeted detection and sequencing of DNA, RNA, and Protein, and more particularly performing this analysis from a single cell.

BACKGROUND

The development of multiomic approaches to studying analytes in a human cell holds many promises for increasing our understanding and for developing new therapies. However, these technologies have yet to fulfil this promise yet due to the complexity of such systems, limitations, road blocks and problems with current methods and systems, such as the low amount of biological sample available from small samples (e.g. cells, or a cell). There is a need for method, system and apparatus to provide high-throughput, single-cell analysis that incorporates targeted, DNA, RNA and protein detection and characterization. There is also a need for a system that can be customized for the detection of particular analytes. The inventions provided here address these unmet needs.

BRIEF SUMMARY

The inventions described and claimed herein have many attributes and embodiments including, but not limited to, those set forth or described or referenced in this Brief Summary. The inventions described and claimed herein are not limited to, or by, the features or embodiments identified in this Summary, which is included for purposes of illustration only and not restriction.

In a first aspect, embodiments of the invention are directed to methods for the simultaneous targeted detection and sequencing of DNA, RNA, and Protein. In preferred embodiments, the DNA, RNA, and proteins are detected, characterized, and sequenced using just a single cell. A multiomic detection and characterization method provided herein may utilize the following novel strategy: i) proteins are tagged with antibodies, ii) RNA is reverse transcribed, iii) DNA is released from the cell nucleus, and iv) each of the preceding is tagged with a cell identifier (e.g. a barcode) so that DNA, RNA, and proteins from the same cell will have the same identifier that is unique to that cell.

One embodiment of a multiomic detection and characterization method for detecting DNA, RNA, or protein from a single cell includes, independent of order, the following steps: encapsulating a cell in a drop comprising a reaction mixture comprising a protease; performing a protease digest on the encapsulated cell drop with the protease to produce a cell lysate; providing a reverse transcriptase and performing a reverse transcription reaction; performing a droplet merger with barcoding PCR reagents and barcoding beads; performing a PCR reaction to attach the cell barcodes to the DNA targeted amplicons, RNA targeted amplicons, and protein tag amplicons, wherein all amplicons from the same emulsion contain the same cell barcode; performing a capture of DNA and RNA amplicons to a solid phase, wherein protein tag amplicons are separated from DNA and RNA amplicons; and detecting and characterizing a DNA, RNA, or protein amplicon by sequencing the cell barcode incorporated into each amplicon. In a preferred embodiment, DNA, RNA, and proteins are detected and characterized. Also, the DNA, RNA, and proteins are detected and characterized from a single cell in preferred embodiments.

In some embodiments, the reverse transcription reaction is performed in the same drop as the protease digest. In other embodiments, a droplet merger with the cell lysate and reverse transcriptase is performed before the reverse transcription reaction is performed. Typically, the protease and reverse transcriptase reactions are performed on a PCR thermocycler and later transferred to another instrument for processing and analysis. The preferred instrument for processing and analysis comprises a Tapestri® (a multiomics workflow) system and the droplet merger with barcoding PCR reagents and barcoding beads is performed on this instrument. In some embodiments, a nucleic acid concentration step is performed.

In one particular exemplary embodiment, a sample of cells is obtained and the cells are stained. The single cells are encapsulated with a buffer containing components for lysis, reverse transcription, and a protease treatment. The reactions are performed on a thermocycler and the encapsulated cells transferred to suitable platform, preferably a Tapestri® (a multiomics workflow) system, to perform a droplet merger with barcoding PCR reagents and barcoding beads. A PCR is performed which attaches the cell barcodes to the DNA targeted amplicons, RNA targeted amplicons, and protein tag amplicons. All amplicons from the same emulsion contain the same cell barcode. After emulsions are broken, an exonuclease reaction, and a SPRI cleanup may be performed. The supernatant is kept to process into protein libraries. The SPRI beads contain both the DNA and RNA amplicons that are then separated using a biotin capture oligo and streptavidin beads. The DNA and RNA amplicons are typically, but not always, processed separately to form sequencing libraries. This embodiment may use a two-droplet process where cells are individually encapsulated in a first droplet where analyte preparation can occur, including aggressive protease digestion and subsequent protease heat inactivation. Afterwards, additional reagents and enzymes can be merged into a second drop in which a barcoding and amplification reaction takes place.

In some embodiments, one or more DNA, RNA, and protein listed in FIG. 9 is detected and characterized. In some embodiments, two or more DNA, RNA, and protein listed in FIG. 9 are detected and characterized. In some embodiments, three or more DNA, RNA, and protein listed in FIG. 9 are detected and characterized. In some embodiments, four or more DNA, RNA, and protein listed in FIG. 9 are detected and characterized. In some embodiments, five or more DNA, RNA, and protein listed in FIG. 9 are detected and characterized. In some embodiments, at least five DNA, RNA, and proteins listed in FIG. 9 are detected and characterized. In some embodiments, at least ten DNA, RNA, and proteins listed in FIG. 9 are detected and characterized. In some embodiments, at least twenty DNA, RNA, and proteins listed in FIG. 9 are detected and characterized.

In another aspect, a method for preparing a protein library and a DNA library which can be paired based on the cell barcode is provided.

In another aspect, a method for preparing a protein library and an RNA library which can be paired based on the cell barcode is provided. These embodiments do not typically utilize a protease treatment as part of the cell preparation.

In another aspect, a method for preparing a protein library, DNA library, and RNA library which can be paired based on the cell barcode is provided.

BRIEF DESCRIPTION OF THE DRAWINGS

FIG. 8 also shows the clustering with t-SNE and umap where the colors are the same as in the heat map.

FIG. 9 also shows those same cells clustered with umap based on SNV, CNV, protein, and RNA where the color of each datapoint corresponds to the cell identified by the mutations found in DNA. The doses of imatinib were differentiated by the tags on the cell hashing antibodies resulting in more clusters for the protein expression.

DETAILED DESCRIPTION

Figure 1:
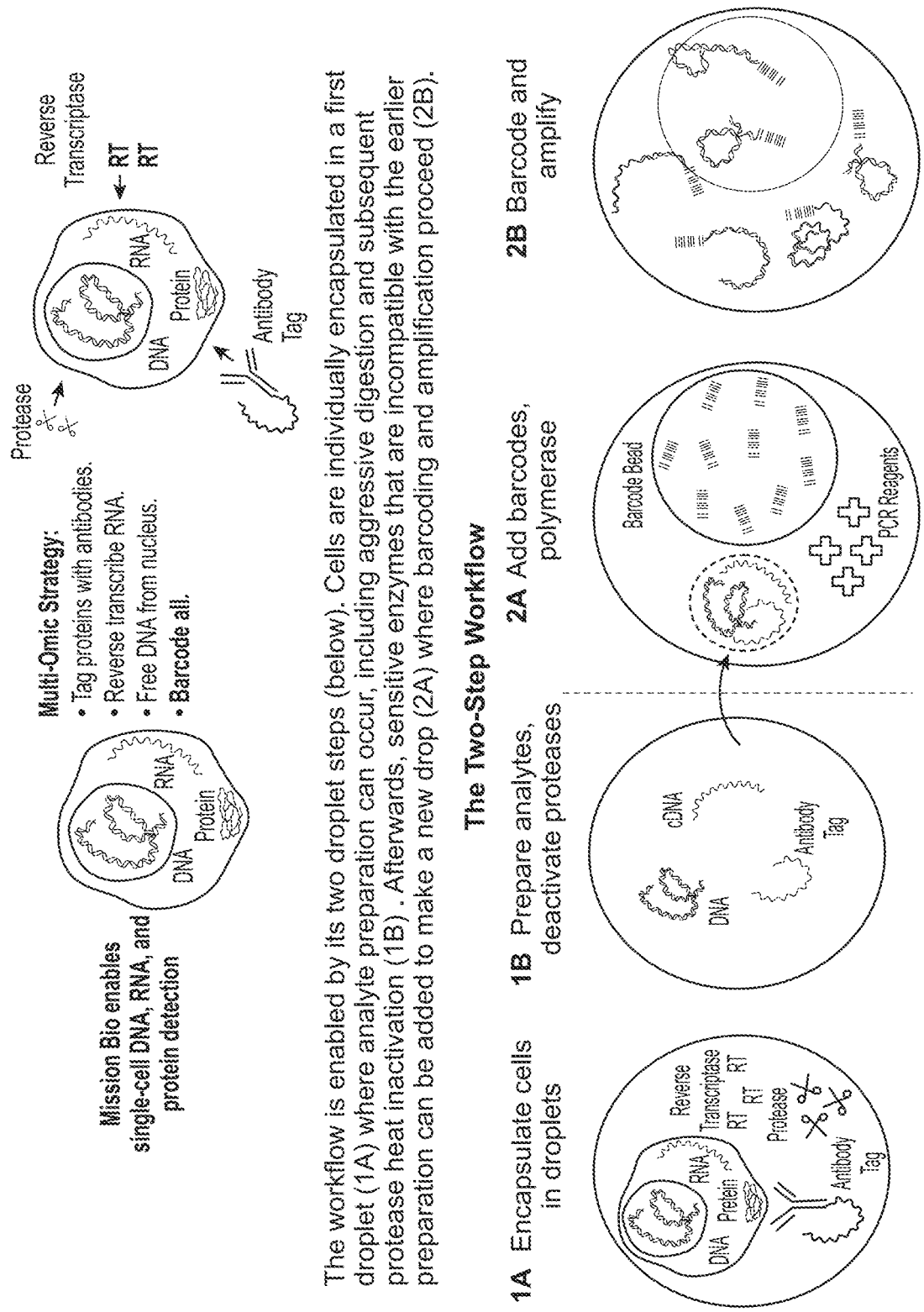
FIG. 1 is a schematic diagram of a multiomic strategy used in some embodiments to detect DNA, RNA, and protein from a single cell.
Figure 2:
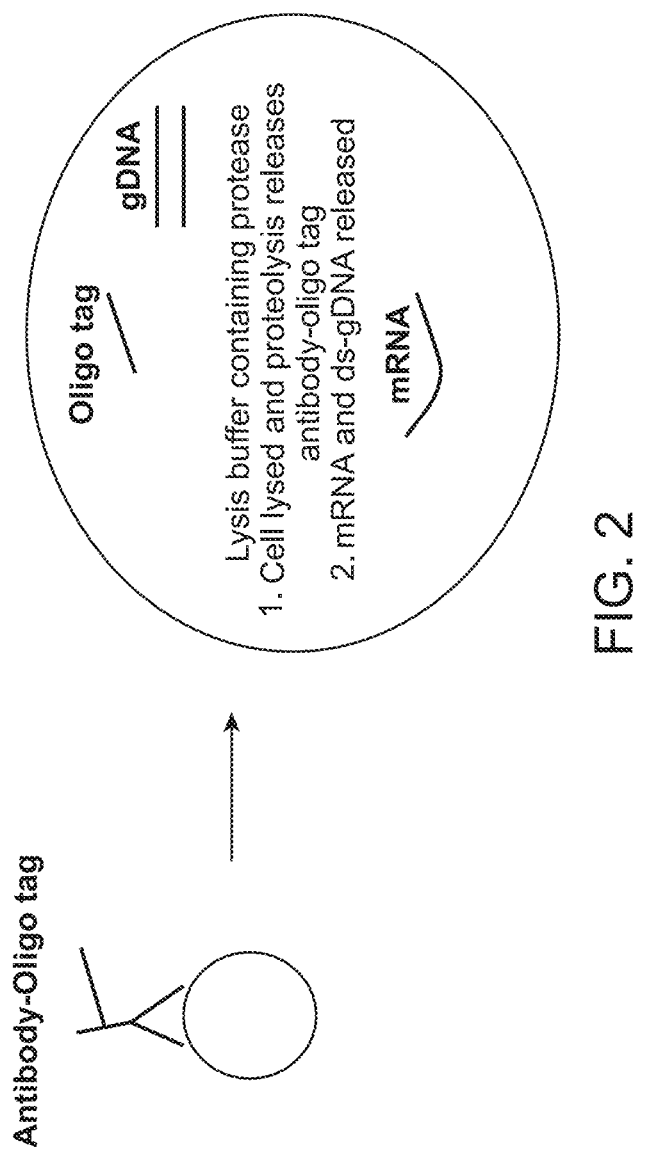
FIG. 2 is a schematic diagram of the first droplet of an exemplary embodiment of the invention.
Figure 3:
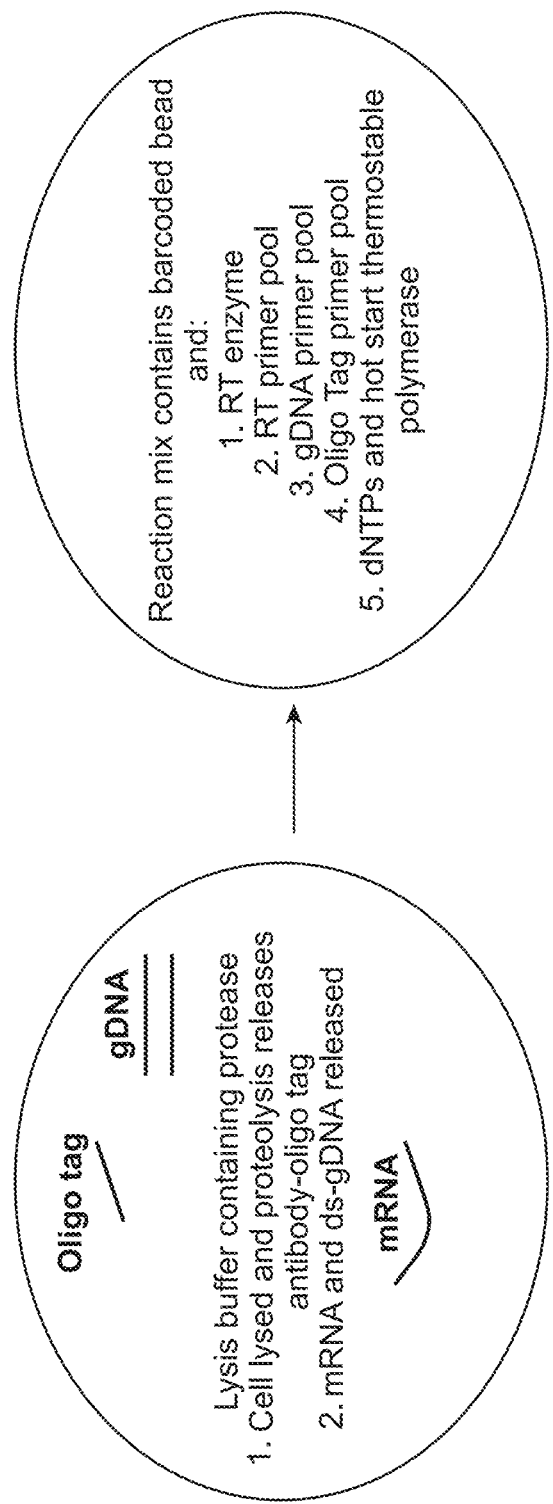
FIG. 3 is a schematic diagram of the second droplet of an exemplary embodiment of the invention.

Various aspects of the invention will now be described with reference to the following section which will be understood to be provided by way of illustration only and not to constitute a limitation on the scope of the invention.

"Complementarity" refers to the ability of a nucleic acid to form hydrogen bond(s) or hybridize with another nucleic acid sequence by either traditional Watson-Crick or other non-traditional types. As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA. See e.g. Ausubel, et al., Current Protocols In Molecular Biology, John Wiley & Sons, New York, N.Y., 1993. If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are "substantially complementary" to each other when a sufficient number of corresponding positions in each molecule are occupied by nucleotides that can hybridize or anneal with each other in order to affect the desired process. A complementary sequence is a sequence capable of annealing under stringent conditions to provide a 3'-terminal serving as the origin of synthesis of complementary chain.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

The terms "amplify", "amplifying", "amplification reaction" and their variants, refer generally to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated, on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR). In the present invention, the terms "synthesis" and "amplification" of nucleic acid are used. The synthesis of nucleic acid in the present invention means the elongation or extension of nucleic acid from an oligonucleotide serving as the origin of synthesis. If not only this synthesis but also the formation of other nucleic acid and the elongation or extension reaction of this formed nucleic acid occur continuously, a series of these reactions is comprehensively called amplification. The polynucleic acid produced by the amplification technology employed is generically referred to as an "amplicon" or "amplification product."

A number of nucleic acid polymerases can be used in the amplification reactions utilized in certain embodiments provided herein, including any enzyme that can catalyze the polymerization of nucleotides (including analogs thereof) into a nucleic acid strand. Such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also includes fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase can be optionally reactivated, for example through the use of heat, chemicals or re-addition of new amounts of polymerase into a reaction mixture. In some embodiments, the polymerase can include a hot-start polymerase or an aptamer-based polymerase that optionally can be reactivated.

The terms "target primer" or "target-specific primer" and variations thereof refer to primers that are complementary to a binding site sequence. Target primers are generally a single stranded or double-stranded polynucleotide, typically an oligonucleotide, that includes at least one sequence that is at least partially complementary to a target nucleic acid sequence.

"Forward primer binding site" and "reverse primer binding site" refers to the regions on the template DNA and/or the amplicon to which the forward and reverse primers bind. The primers act to delimit the region of the original template polynucleotide which is exponentially amplified during amplification. In some embodiments, additional primers may bind to the region 5' of the forward primer and/or reverse primers. Where such additional primers are used, the forward primer binding site and/or the reverse primer binding site may encompass the binding regions of these additional primers as well as the binding regions of the primers themselves. For example, in some embodiments, the method may use one or more additional primers which bind to a region that lies 5' of the forward and/or reverse primer binding region. Such a method was disclosed, for example, in WO0028082 which discloses the use of "displacement primers" or "outer primers".

A 'barcode' nucleic acid identification sequence can be incorporated into a nucleic acid primer or linked to a primer to enable independent sequencing and identification to be associated with one another via a barcode which relates information and identification that originated from molecules that existed within the same sample. There are numerous techniques that can be used to attach barcodes to the nucleic acids within a discrete entity. For example, the target nucleic acids may or may not be first amplified and fragmented into shorter pieces. The molecules can be combined with discrete entities, e.g., droplets, containing the barcodes. The barcodes can then be attached to the molecules using, for example, splicing by overlap extension. In this approach, the initial target molecules can have "adaptor" sequences added, which are molecules of a known sequence to which primers can be synthesized. When combined with the barcodes, primers can be used that are complementary to the adaptor sequences and the barcode sequences, such that the product amplicons of both target nucleic acids and barcodes can anneal to one another and, via an extension reaction such as DNA polymerization, be extended onto one another, generating a double-stranded product including the target nucleic acids attached to the barcode sequence. Alternatively, the primers that amplify that target can themselves be barcoded so that, upon annealing and extending onto the target, the amplicon produced has the barcode sequence incorporated into it. This can be applied with a number of amplification strategies, including specific amplification with PCR or non-specific amplification with, for example, MDA. An alternative enzymatic reaction that can be used to attach barcodes to nucleic acids is ligation, including blunt or sticky end ligation. In this approach, the DNA barcodes are incubated with the nucleic acid targets and ligase enzyme, resulting in the ligation of the barcode to the targets. The ends of the nucleic acids can be modified as needed for ligation by a number of techniques, including by using adaptors introduced with ligase or fragments to enable greater control over the number of barcodes added to the end of the molecule.

A barcode sequence can additionally be incorporated into microfluidic beads to decorate the bead with identical sequence tags. Such tagged beads can be inserted into microfluidic droplets and via droplet PCR amplification, tag each target amplicon with the unique bead barcode. Such barcodes can be used to identify specific droplets upon a population of amplicons originated from. This scheme can be utilized when combining a microfluidic droplet containing single individual cell with another microfluidic droplet containing a tagged bead. Upon collection and combination of many microfluidic droplets, amplicon sequencing results allow for assignment of each product to unique microfluidic droplets. In a typical implementation, we use barcodes on the Tapestri® (a multiomics workflow) beads to tag and then later identify each droplet's amplicon content. The use of barcodes is described in U.S. patent application Ser. No. 15/940,850 filed Mar. 29, 2018 by Abate, A et al., entitled 'Sequencing of Nucleic Acids via Barcoding in Discrete Entities', incorporated by reference herein.

In some embodiments, it may be advantageous to introduce barcodes into discrete entities, e.g., microdroplets, on the surface of a bead, such as a solid polymer bead or a hydrogel bead. These beads can be synthesized using a variety of techniques. For example, using a mix-split technique, beads with many copies of the same, random barcode sequence can be synthesized. This can be accomplished by, for example, creating a plurality of beads including sites on which DNA can be synthesized. The beads can be divided into four collections and each mixed with a buffer that will add a base to it, such as an A, T, G, or C. By dividing the population into four subpopulations, each subpopulation can have one of the bases added to its surface. This reaction can be accomplished in such a way that only a single base is added and no further bases are added. The beads from all four subpopulations can be combined and mixed together, and divided into four populations a second time. In this division step, the beads from the previous four populations may be mixed together randomly. They can then be added to the four different solutions, adding another, random base on the surface of each bead. This process can be repeated to generate sequences on the surface of the bead of a length approximately equal to the number of times that the population is split and mixed. If this was done 10 times, for example, the result would be a population of beads in which each bead has many copies of the same random 10-base sequence synthesized on its surface. The sequence on each bead would be determined by the particular sequence of reactors it ended up in through each mix-spit cycle.

A barcode may further comprise a 'unique identification sequence' (UMI). A UMI is a nucleic acid having a sequence which can be used to identify and/or distinguish one or more first molecules to which the UMI is conjugated from one or more second molecules. UMIs are typically short, e.g., about 5 to 20 bases in length, and may be conjugated to one or more target molecules of interest or amplification products thereof. UMIs may be single or double stranded. In some embodiments, both a nucleic acid barcode sequence and a UMI are incorporated into a nucleic acid target molecule or an amplification product thereof. Generally, a UMI is used to distinguish between molecules of a similar type within a population or group, whereas a nucleic acid barcode sequence is used to distinguish between populations or groups of molecules. In some embodiments, where both a UMI and a nucleic acid barcode sequence are utilized, the UMI is shorter in sequence length than the nucleic acid barcode sequence.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 97%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443

(1970), etc. Another indication that two nucleic acid sequences are substantially identical is that the two molecules or their complements hybridize to each other under stringent hybridization conditions.

The terms "nucleic acid," "polynucleotides," and "oligonucleotides" refers to biopolymers of nucleotides and, unless the context indicates otherwise, includes modified and unmodified nucleotides, and both DNA and RNA, and modified nucleic acid backbones. For example, in certain embodiments, the nucleic acid is a peptide nucleic acid (PNA) or a locked nucleic acid (LNA). Typically, the methods as described herein are performed using DNA as the nucleic acid template for amplification. However, nucleic acid whose nucleotide is replaced by an artificial derivative or modified nucleic acid from natural DNA or RNA is also included in the nucleic acid of the present invention insofar as it functions as a template for synthesis of complementary chain. The nucleic acid of the present invention is generally contained in a biological sample. The biological sample includes animal, plant or microbial tissues, cells, cultures and excretions, or extracts therefrom. In certain aspects, the biological sample includes intracellular parasitic genomic DNA or RNA such as virus or mycoplasma. The nucleic acid may be derived from nucleic acid contained in said biological sample. For example, genomic DNA, or cDNA synthesized from mRNA, or nucleic acid amplified on the basis of nucleic acid derived from the biological sample, are preferably used in the described methods. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U' denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

A template nucleic acid is a nucleic acid serving as a template for synthesizing a complementary chain in a nucleic acid amplification technique. A complementary chain having a nucleotide sequence complementary to the template has a meaning as a chain corresponding to the template, but the relationship between the two is merely relative. That is, according to the methods described herein a chain synthesized as the complementary chain can function again as a template. That is, the complementary chain can become a template. In certain embodiments, the template is derived from a biological sample, e.g., plant, animal, virus, micro-organism, bacteria, fungus, etc. In certain embodiments, the animal is a mammal, e.g., a human patient. A template nucleic acid typically comprises one or more target nucleic acid. A target nucleic acid in exemplary embodiments may comprise any single or double-stranded nucleic acid sequence that can be amplified or synthesized according to the disclosure, including any nucleic acid sequence suspected or expected to be present in a sample.

Primers and oligonucleotides used in embodiments herein comprise nucleotides. A nucleotide comprises any compound, including without limitation any naturally occurring nucleotide or analog thereof, which can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. For example, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, BH3, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281.

In some embodiments, the nucleotide comprises a label and referred to herein as a "labeled nucleotide"; the label of the labeled nucleotide is referred to herein as a "nucleotide label". In some embodiments, the label can be in the form of a fluorescent moiety (e.g. dye), luminescent moiety, or the like attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. α-thio-nucleotide 5'-triphosphates. For a review of nucleic acid chemistry, see: Shabarova, Z. and Bogdanov, A. Advanced Organic Chemistry of Nucleic Acids, VCH, New York, 1994.

Any nucleic acid amplification method may be utilized, such as a PCR-based assay, e.g., quantitative PCR (qPCR), or an isothermal amplification may be used to detect the presence of certain nucleic acids, e.g., genes, of interest, present in discrete entities or one or more components thereof, e.g., cells encapsulated therein. Such assays can be applied to discrete entities within a microfluidic device or a portion thereof or any other suitable location. The conditions of such amplification or PCR-based assays may include detecting nucleic acid amplification over time and may vary in one or more ways.

The number of amplification/PCR primers that may be added to a microdroplet may vary. The number of amplification or PCR primers that may be added to a microdroplet may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

One or both primer of a primer set may also be attached or conjugated to an affinity reagent that may comprise anything that binds to a target molecule or moiety. Nonlimiting examples of affinity reagent include ligands, receptors, antibodies and binding fragments thereof, peptide, nucleic acid, and fusions of the preceding and other small molecule that specifically binds to a larger target molecule in order to identify, track, capture, or influence its activity. Affinity reagents may also be attached to solid supports, beads, discrete entities, or the like, and are still referenced as affinity reagents herein.

One or both primers of a primer set may comprise a barcode sequence described herein. In some embodiments, individual cells, for example, are isolated in discrete entities, e.g., droplets. These cells may be lysed and their nucleic acids barcoded. This process can be performed on a large number of single cells in discrete entities with unique barcode sequences enabling subsequent deconvolution of mixed sequence reads by barcode to obtain single cell information. This approach provides a way to group together nucleic acids originating from large numbers of single cells. Additionally, affinity reagents such as antibodies can be conjugated with nucleic acid labels, e.g., oligonucleotides including barcodes, which can be used to identify antibody type, e.g., the target specificity of an antibody. These reagents can then be used to bind to the proteins within or on cells, thereby associating the nucleic acids carried by the affinity reagents to the cells to which they are bound. These cells can then be processed through a barcoding workflow as described herein to attach barcodes to the nucleic acid labels on the affinity reagents. Techniques of library preparation, sequencing, and bioinformatics may then be used to group the sequences according to cell/discrete entity barcodes. Any suitable affinity reagent that can bind to or recognize a biological sample or portion or component thereof, such as a protein, a molecule, or complexes thereof, may be utilized in connection with these methods. The affinity reagents may be labeled with nucleic acid sequences that relates their identity, e.g., the target specificity of the antibodies, permitting their detection and quantitation using the barcoding and sequencing methods described herein. Exemplary affinity reagents can include, for example, antibodies, antibody fragments, Fabs, scFvs, peptides, drugs, etc. or combinations thereof. The affinity reagents, e.g., antibodies, can be expressed by one or more organisms or provided using a biological synthesis technique, such as phage, mRNA, or ribosome display. The affinity reagents may also be generated via chemical or biochemical means, such as by chemical linkage using N-Hydroxysuccinimide (NETS), click chemistry, or streptavidin-biotin interaction, for example. The oligo-affinity reagent conjugates can also be generated by attaching oligos to affinity reagents and hybridizing, ligating, and/or extending via polymerase, etc., additional oligos to the previously conjugated oligos. An advantage of affinity reagent labeling with nucleic acids is that it permits highly multiplexed analysis of biological samples. For example, large mixtures of antibodies or binding reagents recognizing a variety of targets in a sample can be mixed together, each labeled with its own nucleic acid sequence. This cocktail can then be reacted to the sample and subjected to a barcoding workflow as described herein to recover information about which reagents bound, their quantity, and how this varies among the different entities in the sample, such as among single cells. The above approach can be applied to a variety of molecular targets, including samples including one or more of cells, peptides, proteins, macromolecules, macromolecular complexes, etc. The sample can be subjected to conventional processing for analysis, such as fixation and permeabilization, aiding binding of the affinity reagents. To obtain highly accurate quantitation, the unique molecular identifier (UMI) techniques described herein can also be used so that affinity reagent molecules are counted accurately. This can be accomplished in a number of ways, including by synthesizing UMIs onto the labels attached to each affinity reagent before, during, or after conjugation, or by attaching the UMIs microfluidically when the reagents are used. Similar methods of generating the barcodes, for example, using combinatorial barcode techniques as applied to single cell sequencing and described herein, are applicable to the affinity reagent technique. These techniques enable the analysis of proteins and/or epitopes in a variety of biological samples to perform, for example, mapping of epitopes or post translational modifications in proteins and other entities or performing single cell proteomics. For example, using the methods described herein, it is possible to generate a library of labeled affinity reagents that detect an epitope in all proteins in the proteome of an organism, label those epitopes with the reagents, and apply the barcoding and sequencing techniques described herein to detect and accurately quantitate the labels associated with these epitopes.

Primers may contain primers for one or more nucleic acid of interest, e.g. one or more genes of interest. The number of primers for genes of interest that are added may be from about one to 500, e.g., about 1 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more. Primers and/or reagents may be added to a discrete entity, e.g., a microdroplet, in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, the PCR primers may be added in a separate step from the addition of a lysing agent. In some embodiments, the discrete entity, e.g., a microdroplet, may be subjected to a dilution step and/or enzyme inactivation step prior to the addition of the PCR reagents. Exemplary embodiments of such methods are described in PCT Publication No. WO 2014/028378, the disclosure of which is incorporated by reference herein in its entirety and for all purposes.

A primer set for the amplification of a target nucleic acid typically includes a forward primer and a reverse primer that are complementary to a target nucleic acid or the complement thereof. In some embodiments, amplification can be performed using multiple target-specific primer pairs in a single amplification reaction, wherein each primer pair includes a forward target-specific primer and a reverse target-specific primer, where each includes at least one sequence that substantially complementary or substantially identical to a corresponding target sequence in the sample, and each primer pair having a different corresponding target sequence. Accordingly, certain methods herein are used to detect or identify multiple target sequences from a single cell sample.

In some implementations, solid supports, beads, and the like are coated with affinity reagents. Affinity reagents include, without limitation, antigens, antibodies or aptamers with specific binding affinity for a target molecule. The affinity reagents bind to one or more targets within the single cell entities. Affinity reagents are often detectably labeled (e.g., with a fluorophore). Affinity reagents are sometimes labeled with unique barcodes, oligonucleotide sequences, or UMI's.

In some implementations, a RT/PCR polymerase reaction and amplification reaction are performed, for example in the same reaction mixture, as an addition to the reaction mixture, or added to a portion of the reaction mixture.

In one particular implementation, a solid support contains a plurality of affinity reagents, each specific for a different target molecule but containing a common sequence to be used to identify the unique solid support. Affinity reagents that bind a specific target molecule are collectively labeled with the same oligonucleotide sequence such that affinity molecules with different binding affinities for different targets are labeled with different oligonucleotide sequences. In this way, target molecules within a single target entity are differentially labeled in these implements to determine which target entity they are from but contain a common sequence to identify them from the same solid support.

Targeted Detection and Sequencing of DNA, RNA, and Protein

A first objective of some implementations is to provide methods for the simultaneous targeted detection and sequencing of DNA, RNA, and Protein. In preferred embodiments, the DNA, RNA, and Protein is detected, characterized, and sequenced using single cells. Single-cell analysis is conducted herein by sequencing either genomic DNA targets, RNA/cDNA transcripts or protein detection. Genomic DNA can be assessed by first amplifying whole genomic DNA or targeted approaches.

One such example is amplifying whole genomic DNA or targeted portions of the DNA in a Tapestri® (a multiomics workflow) platform. In some embodiments using this approach, RNA/cDNA transcripts are often accessed by first priming with 3' mRNA end oligo dT extension strategies or random primers. Targeted cDNA extension can be conducted using transcript specific primers and is amenable to these workflows. Surface protein markers are readily detected using dye-labelled antibodies and a fluorescence-activated cell sorting platform (FACS). In preferred embodiments, DNA barcoded antibodies can be employed in cell staining and readout by next generation sequencing (NGS).

We have combined three different methodologies to simultaneously detect, by targeted sequencing, DNA, RNA, and surface protein markers as our so-called 'triomic' methodology. Our novel approach represents a great advancement in single-cell analysis.

Typically, methods are optimized to efficiently detect and amplify genomic DNA amplicon targets. Additionally, some implementations use reverse transcriptase enzyme with RNA-specific primers to extend RNA targets and generate cDNA templates for efficient RNA detection. Additionally, an antibody-oligonucleotide tagging system for surface protein detection on single-cells using microfluidic droplets has been developed. In certain embodiments provided herein, a Tapestri® (a multiomics workflow) workflow scheme has been developed that applies central concepts from all three 'omics' to thereby provide for a triomic interrogation process for single-cells. While the disclosed embodiments relate to using the Tapestri® (a multiomics workflow) workflow, it should be noted that the disclosed principles are not limited thereto and may be applied to other instrumentations and/or workflow.

Certain methods provided herein utilize specific antibodies to detect epitopes of interest. In some embodiments, antibodies are labeled with sequence tags that can be read out with microfluidic barcoding and DNA sequencing. This and related implementations are used herein to characterize cell surface proteins of different cell types at the single-cell level.

In some embodiments, a barcode identity is encoded by its full nucleobase sequence and thus confers a combinatorial tag space far exceeding what is possible with conventional approaches using fluorescence. A modest tag length of ten bases provides over a million unique sequences, sufficient to label an antibody against every epitope in the human proteome. Indeed, with this approach, the limit to multiplexing is not the availability of unique tag sequences but, rather, that of specific antibodies that can detect the epitopes of interest in a multiplexed reaction.

In some implementations, cells are bound with antibodies against the different target epitopes, as in conventional immunostaining, except that the antibodies are labeled with barcodes.

In practice, when an antibody binds its target the DNA barcode tag is carried with it and thus allows the presence of the target to be inferred based on the presence of the barcode. In some implementations, counting barcode tags provides an estimate of the different epitopes present in the cell.

Other embodiments implementations are used to distinguish particular cells by their protein expression profiles. Some embodiments of DNA-tagged antibodies provided herein have multiple advantages for profiling proteins in single cells.

A primary advantage of these implementations is the ability to amplify low-abundance tags to make them detectable with sequencing. Another advantage in some implementations is the capability of using molecular indices for quantitative results. Some implementations also have essentially limitless multiplexing capabilities.

Some embodiments utilize solid beads having an alternate chemistry where the primers to be used are in solution and contain a PCR annealing sequence embedded, or 'handle', that allows hybridization to primers. In some implementations, the handle is a specific tail 5' upstream of the target sequence and this handle is complimentary to bead barcoded oligo and serves as a PCR extension bridge to link the target amplicon to the bead barcode library primer sequence. The solid beads may contain primers that can anneal to the PCR handle on the primers.

Some embodiments are used to detect and characterize cell surface proteins, DNA, and RNA. Such a workflow can begin with an antibody-oligonucleotide staining and washing of a single-cell suspension. The stained cells are loaded onto a Tapestri® (a multiomics workflow) system, cells are lysed, RNA is converted to cDNA by reverse transcriptase, PCR cycling is used to amplify antibody-oligonucleotides, targeted cDNA species, and targeted genomic DNA regions. All three omic libraries are purified and quantified, and sequencing is conducted to determine the identity of an analyte. This workflow is only exemplary, and it is understood that certain steps can be removed and other steps can be added.

Other aspects of the invention may be described in the follow embodiments:

1. An apparatus or system for performing a method described herein.
2. A composition or reaction mixture for performing a method described herein.
3. An antibody library generated by methods described herein.
4. A genomic library generated by methods described herein.
5. A transcriptome library generated according to a method described herein.
6. An antibody library, genomic, and transcriptome library generated according to a method described herein.
7. A kit for performing a method described herein.
8. A cell population selected by the methods described herein.
9. A method of determining and characterizing the protein expression pattern of a single cell, the method comprising the steps of:
   a) conjugating barcode sequences flanked by PCR priming sites onto antibodies, wherein a barcode sequence is specific to an antibody;
   b) performing a cell identification step using the barcode conjugated antibodies;
   c) partitioning or separating individual cells and encapsulating one or more individual cell(s) in a reaction mixture comprising a protease;
   d) incubating the encapsulated cell with the protease in the drop to produce a cell lysate;
   e) performing a reverse transcriptase reaction, wherein a reverse transcriptase is in the reaction mixture or added to the reaction mixture
   f) providing one or more nucleic acid amplification primer sets targeting nucleic acids present in a cell, wherein one or more primer of a primer set includes a barcode identification sequence associated with an antibody;
   g) providing one or more nucleic acid amplification primer sets targeting nucleic acids present in a cell, wherein one or more primer of a primer set includes a barcode identification sequence unique to each cell;
   h) performing a nucleic acid amplification reaction to produce one or more amplicons;
   i) providing an affinity reagent that comprises a nucleic acid sequence complementary to the identification barcode sequence of one of more nucleic acid primer of a primer set, wherein said affinity reagent comprising said nucleic acid sequence complementary to the identification barcode sequence is capable of binding to a nucleic acid amplification primer set comprising a barcode identification sequence;
   j) contacting an affinity reagent to the amplification product comprising amplicons of one or more target nucleic acid sequence under conditions sufficient for binding of the affinity reagent to the target nucleic acid to form an affinity reagent bound target nucleic acid; and
   k) determining the identity and characterizing one or more protein by sequencing a barcode of an amplicon.
10. A method for adding a barcode identification sequence linked to an antibody, the method comprising the steps:
   i) performing a barcoding PCR reaction of a target gDNA using a) a primer containing a cell barcode sequence and a PCR handle; b) a primer containing sequence complementary to the target genomic DNA and a PCR handle that is complementary to the primer containing the cell barcode and c) a reverse primer comprising a sequence complementary to the target genomic DNA, an antibody tag sequence, a second PCR handle, and could include a unique molecular tag, to produce an amplicon comprising a cell barcode, a target DNA sequence, an antibody tag with a PCR handle on both the 5' end and 3' end; and
   ii) performing a library creation PCR reaction using a first primers comprising sequencing adapters, sample indexes, and sequences complementary to the two PCR handles produced on the amplicon to produce library comprising sequencing adapters, dual or single sample indexes, a cell barcode, a target DNA sequence, an antibody tag, and could include a unique molecular tag.
11. A method for adding a barcode identification sequence linked to an antibody, the method comprising the steps:
   i) performing a barcoding PCR reaction of a target gDNA using a) a primer containing a cell barcode sequence and a PCR handle; b) a primer containing sequence complementary to the target genomic DNA and a PCR handle that is complementary to the primer containing the cell barcode and c) a reverse primer comprising a sequence complementary to the target genomic DNA, an antibody tag sequence, a second PCR handle, and could include a unique molecular tag, to produce an amplicon comprising a cell barcode, a target DNA sequence, an antibody tag with a PCR handle on both the 5' end and 3' end, a first read sequence a first cell barcode, a constant region 1, a second cell bar code, a constant region 2, the forward primer sequence, an insert sequence of length 'n', a reverse primer comprising a sequence complementary to the target genomic DNA, a unique molecular identifier, an antibody tag sequence, to a second unique molecular identifier; a second read sequence; and
   ii) performing a library creation PCR reaction using a first primers comprising sequencing adapters, sample indexes, and sequences complementary to the two PCR handles produced on the amplicon comprising a P5 sequence and a second read sequence and a second primer comprising a second read sequence, and index sequence, and a P7 sequence to produce library comprising sequencing adapters, dual or single sample indexes, a cell bar code, a target DNA sequence, an antibody tag, and could include a unique molecular tag.

The following Examples are included for illustration and not limitation.

Example I

In this Example, we provide an embodiment for a single workflow for the simultaneous detection of DNA, RNA, and protein as described in FIG. 1. Fresh Jurkat cells, K-562 cells, and KCL-22 cells were treated with imatinib at doses of 10 uM, 100 uM, and 250 uM or left untreated. The cells from each dose were then mixed in equal ratios and stained with the antibodies listed in Table 1 as well as two antibodies for cell hashing, B2M and CD298.

TABLE 2

The 66 genes targeted by 66 RNA amplicons in the multi-omics experiment from Example I.

| CCND3 | CREB5 | HIF1A | NFKB1 | SIRT1 | SRF |
|---|---|---|---|---|---|
| CD44 | CREB1 | HSPB1 | MYC | NCL | TP53 |
| CCND1 | ELK1 | IKBKG | PIK3CB | RHOA | CASP9 |
| CD33 | FOS | IRF9 | PIM1 | MCM4 | CASP3 |
| CDK6 | FHL1 | BCL2 | PIAS1 | NASP | CASP8 |
| CDK4 | FASLG | BCL2L11 | PRKCB | SOS1 | UBB |
| CDKN1B | GNG12 | MAP2K1 | PTEN | TCL1B | MRPL16 |
| CREB3L4 | GSK3B | MAPK1 | HSPA1A | SOCS3 | MRPL21 |
| CDKN1A | BAD | BCL2L1 | HSPA2 | SOCS2 | FAM32A |
| CREBBP | FOXO4 | MYB | IL2RB | STAT4 | ABCB7 |
| CREB3L1 | FOXO1 | NF1 | IL2RA | STAT6 | PCBP1 |

TABLE 3

The 44 genes targeted by 88 DNA amplicons in the multi-omics experiment from Example I.

| EPS15 | PIK3CA | WRN | ARHGEF12 | BUB1B | METTL23 | EP300 |
|---|---|---|---|---|---|---|
| NRAS | MAP3K13 | JAK2 | KRAS | PALB2 | SRSF2 | SSX1 |
| RPS27A | NSD1 | GATA3 | COL2A1 | FANCA | | MFSD11 |
| AFF3 | PTPRK | DKK1 | KMT2D | NCOR1 | DNM2 | |
| PAX3 | CARD11 | POLA2 | CLIP1 | ERBB2 | CIC | |
| CMTM6 | EGFR | CCND1 | FLT3 | KAT2A | BCR | |
| RHOA | EZH2 | ATM | BRCA2 | RAB5C | MYH9 | |

TABLE 1

The 17 protein targets used in the multi-omics experiment from Example I.

| CD14 | CD117 | CD45RA |
|---|---|---|
| CD33 | CD123 | Mouse IgG |
| CD44 | HLA-DR | Annexin V |
| CD38 | CD90 | |
| CD4 | CD34 | |
| CD3 | CD7 | |
| EPCAM | CD45 | |

After staining, 100,000 cells were loaded onto a Tapestri® (a multiomics workflow) instrument for each encapsulation. The encapsulation partitioned single cells along with reagents for cell lysis, reverse transcription, and a protease treatment. The reverse transcription targets are listed in Table 2. Gene specific priming was used for reverse transcription with a reverse transcriptase, such as SuperScript® IV First-Strand Synthesis System. After protease treatment, the encapsulation droplets were then reloaded onto the Tapestri® (a multiomics workflow) instrument for barcoding PCR. The gDNA from each cell were targeted by the 88 amplicons listed in Table 3. Barcoding PCR was performed using the reagents from the Tapestri® (a multiomics workflow) Single-Cell DNA Sequencing V2 kit.

Figure 4:
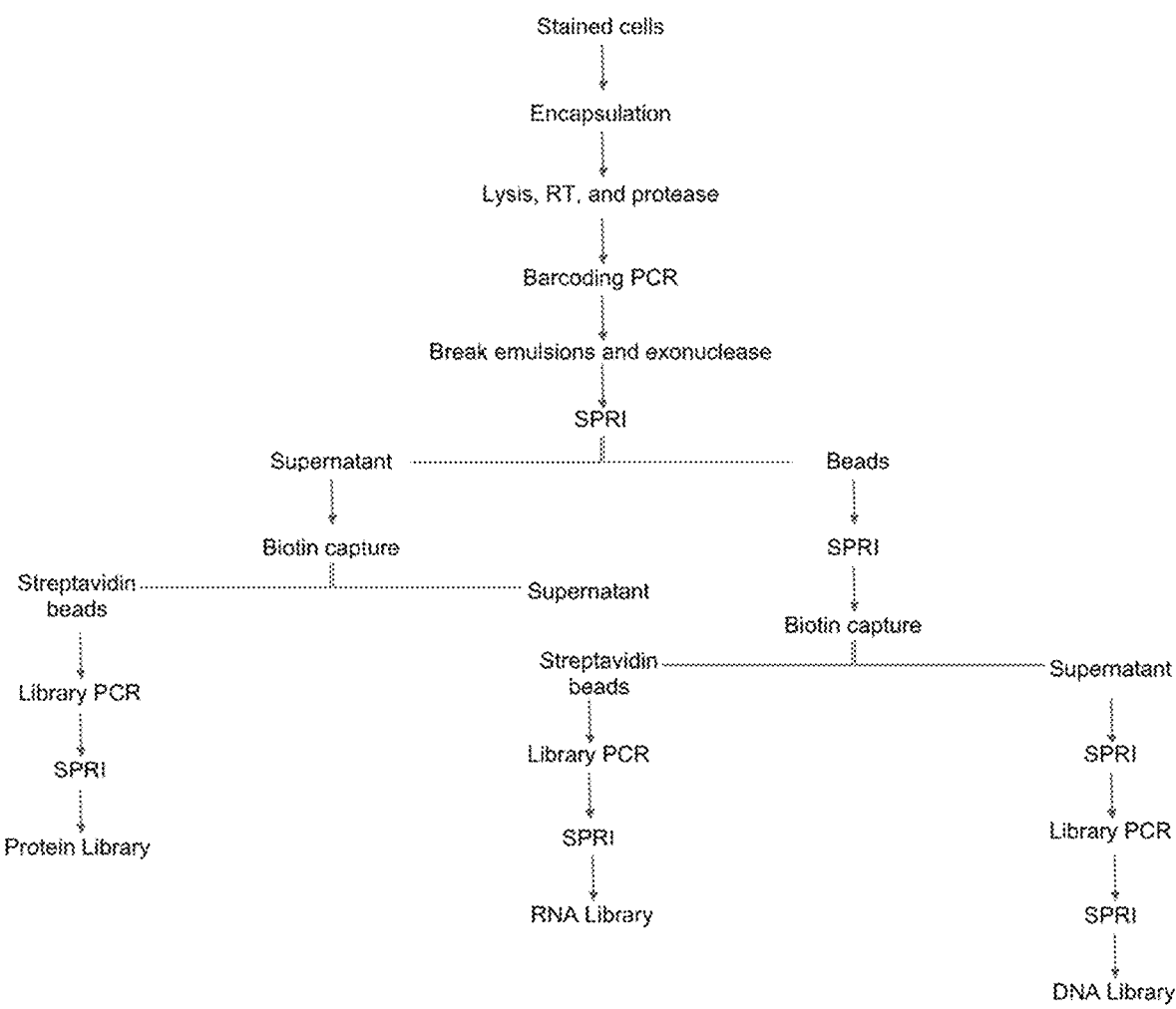
FIG. 4 is a schematic diagram of the multiomics workflow. Stained cells are input onto the Tapestri® (a multiomics workflow) platform. The single cells are encapsulated with a buffer containing components for lysis, reverse transcription, and a protease treatment. These reactions are performed on a thermocycler and the encapsulated cells returned to the Tapestri® (a multiomics workflow) platform to for droplet merger with barcoding PCR reagents and barcoding beads. A PCR is performed which attaches the cell barcodes to the DNA targeted amplicons, RNA targeted amplicons, and protein tag amplicons. All amplicons from the same emulsion would contain the same cell barcode. After emulsions are broken, an exonuclease reaction and a SPRI cleanup are performed. The supernatant is kept to process into protein libraries. The SPRI beads contain both the DNA and RNA amplicons that are then separated using a biotin capture oligo and streptavidin beads. The DNA and RNA amplicons are then processed separately to form sequencing libraries.
Figure 5:
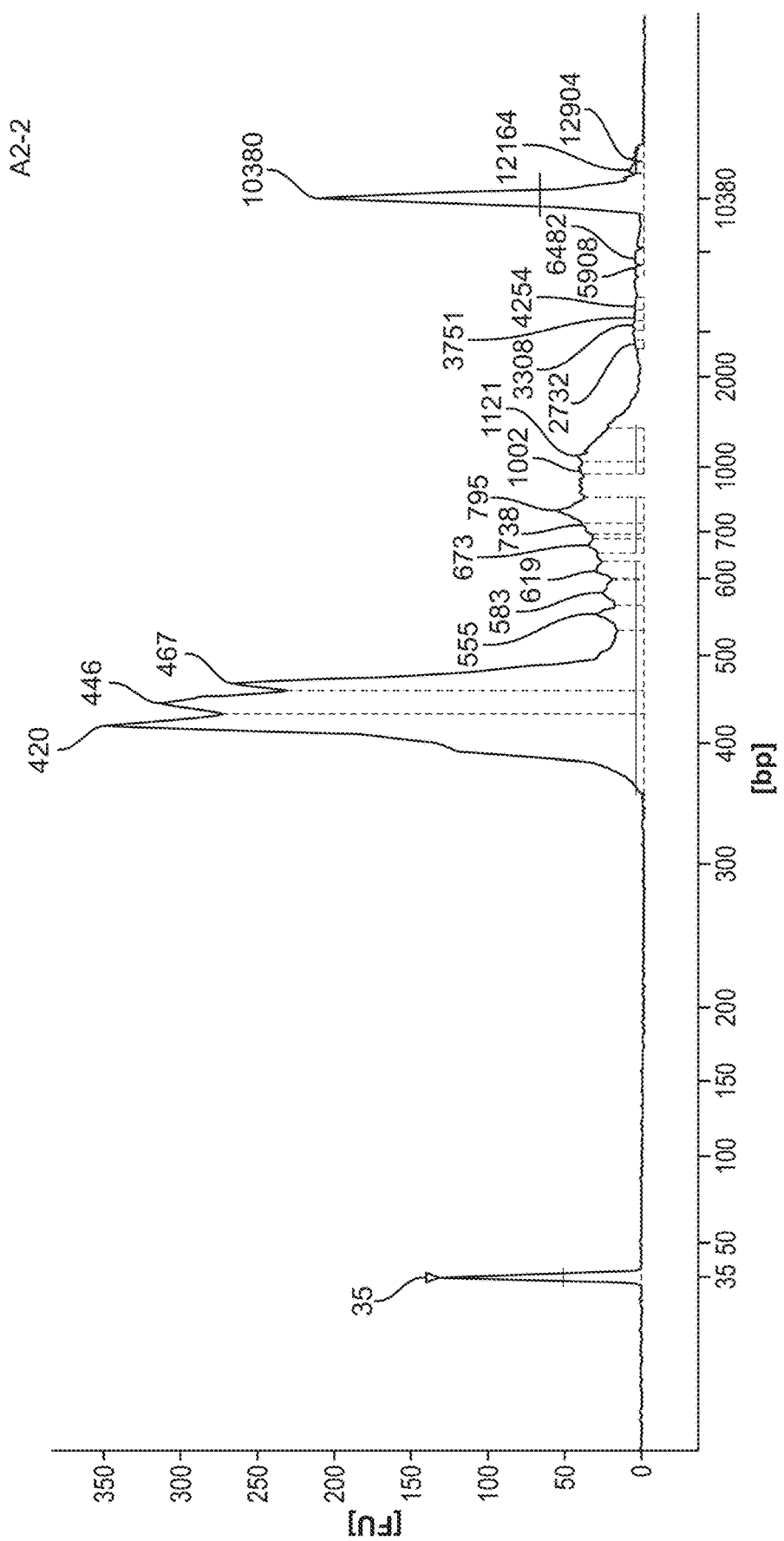
FIG. 5 is Bioanalyzer trace of a DNA library from the untreated cells in tubes 4-8 from the multiomics experiment from Example I where 3 cell lines (Jurkat, K-562, and KCL-22) were untreated or treated 3 different doses of imatinib (10 uM, 100 uM, and 250 uM). 1 uL of undiluted library was loaded onto a HS DNA chip.
Figure 6:
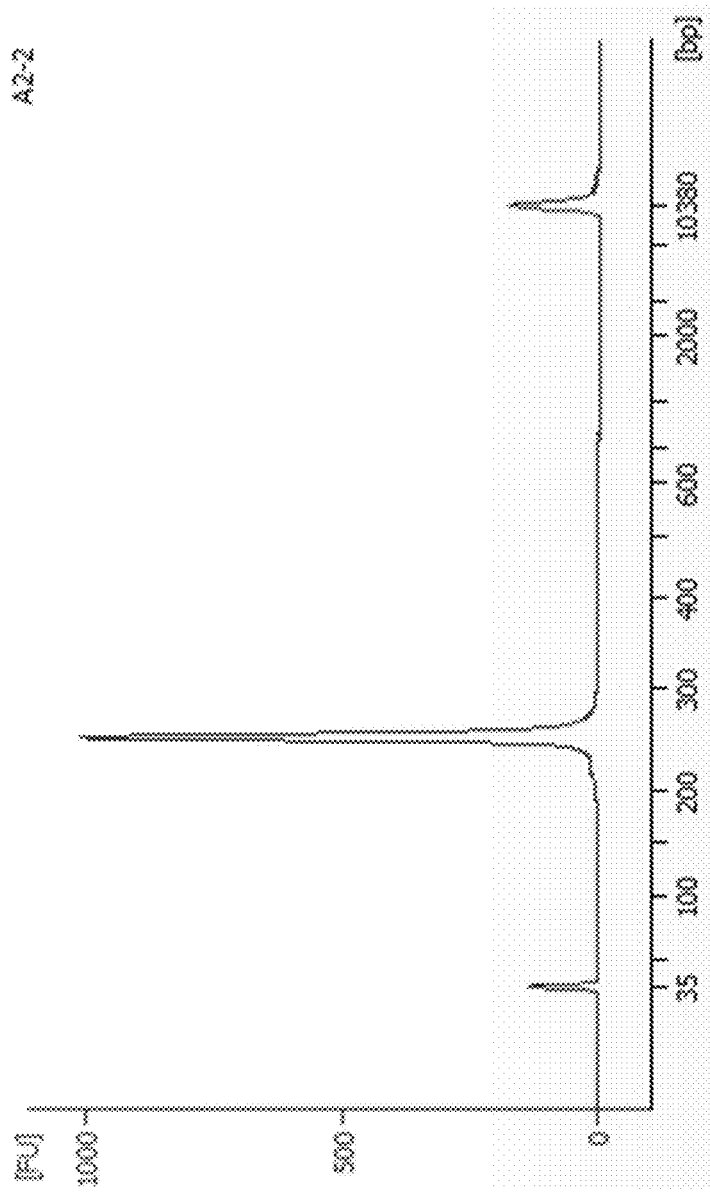
FIG. 6 is Bioanalyzer trace of a protein library from the untreated cells in tubes 4-8 from the multiomics experiment from Example I where 3 cell lines (Jurkat, K-562, and KCL-22) were untreated or treated 3 different doses of imatinib (10 uM, 100 uM, and 250 uM), 1 uL of undiluted library was loaded onto a HS DNA chip.
Figure 7:
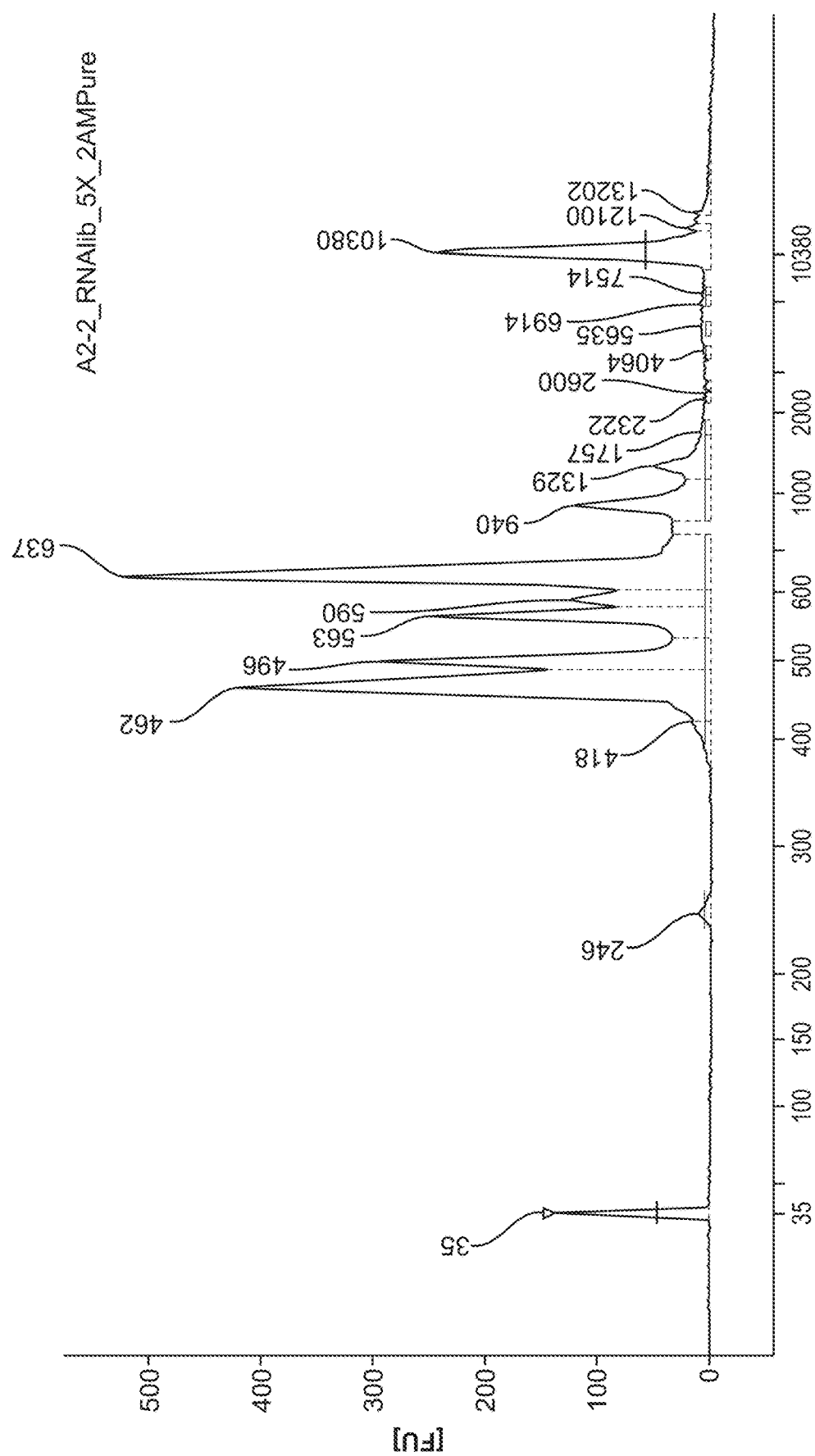
FIG. 7 is a Bioanalyzer trace of a RNA library from the untreated cells in tubes 4-8 from the multiomics experiment from Example I where 3 cell lines (Jurkat, K-562, and KCL-22) were untreated or treated 3 different doses of imatinib (10 uM, 100 uM, and 250 uM). 1 uL of a 1:5 library dilution was loaded onto a HS DNA chip.
Figure 8:
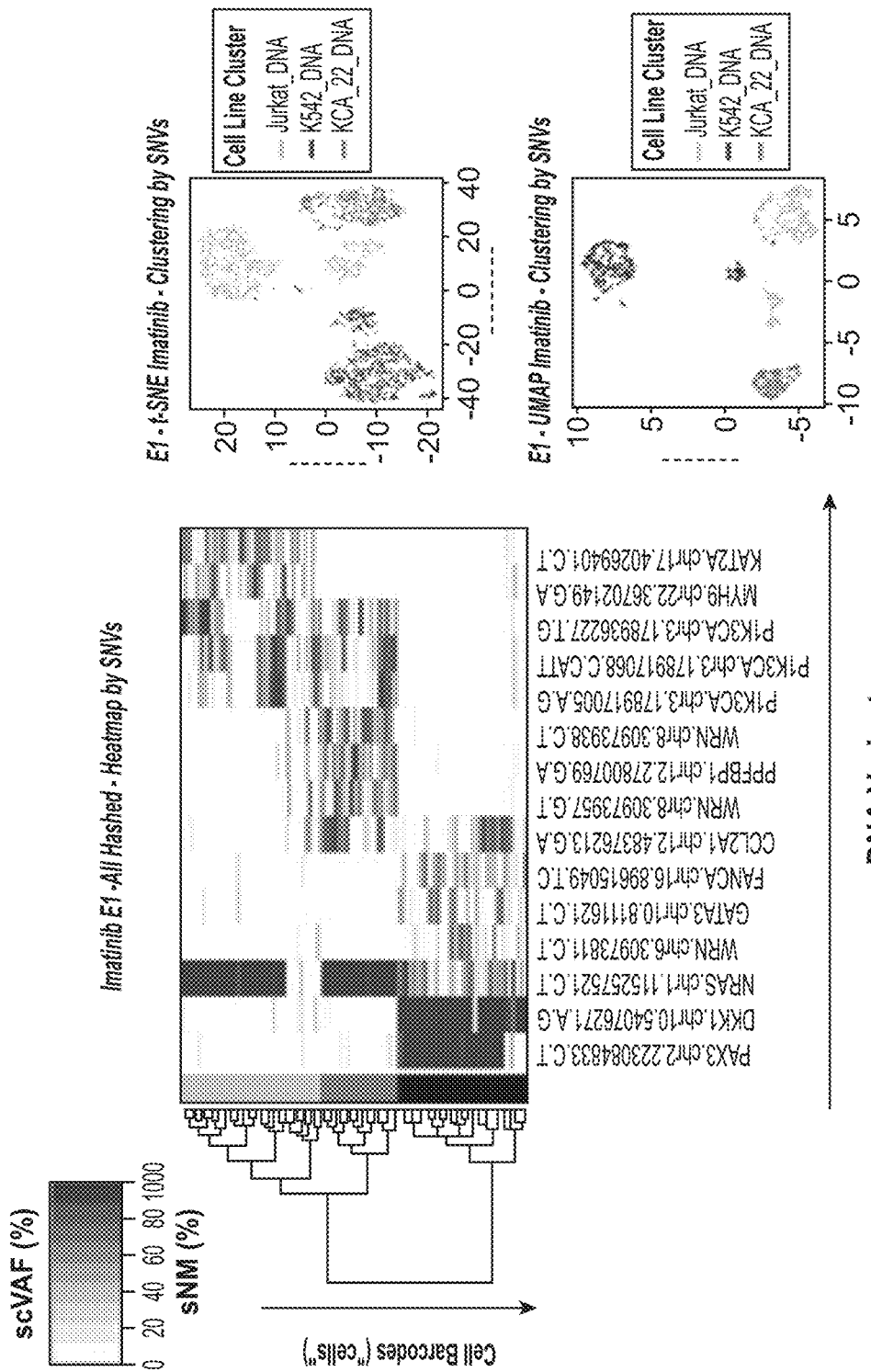
FIG. 8 shows the results from the multiomics experiment from Example 1 where 3 cell lines (Jurkat, K-562, and KCL-22) were untreated or treated 3 different doses of imatinib (10 uM, 100 uM, and 250 uM). The DNA variants are used to make a heat map where the Y-axis are the cell barcodes are shown in FIG. 9. This heat map separates into 3 clusters (green, red, and black, which alternately can be represented as grey shades) which corresponds to each of the cell lines.
Figure 9:
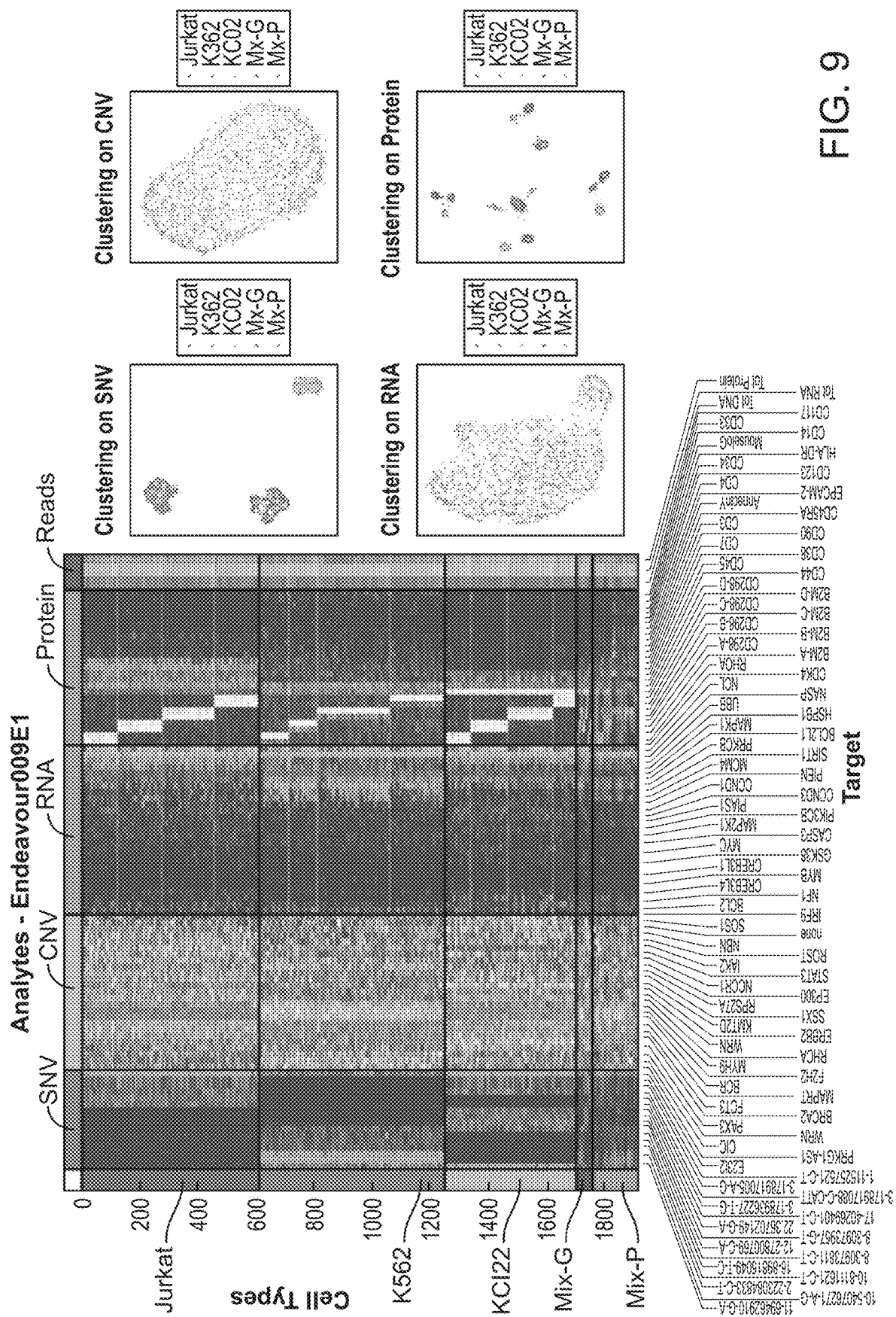
FIG. 9 depicts the results from the multiomics experiment from Example 1 where 3 cell lines (Jurkat, K-562, and KCL-22) were untreated or treated 3 different doses of imatinib (10 uM, 100 uM, and 250 uM). These cells were stained then input onto the Tapestri® (a multiomics workflow) for the multiomics workflow. DNA libraries, RNA libraries, and protein libraries from single cells were produced where the libraries produced from the same cell shared a cell barcode. By looking at the mutations found in the DNA libraries, the 3 cell lines were identified. Each cell barcode also has corresponding RNA reads and protein reads.

After barcoding PCR, sequencing libraries were made separating out the protein libraries, RNA libraries, and DNA libraries as described in FIG. 4. The bioanalyzer traces from the untreated cells are shown in FIGS. 5 (DNA), 6 (protein), and 7 (RNA). These libraries were pooled and sequenced. Each sequencing read with the same cell barcode sequence was identified as being from the same cell. Reads from DNA, RNA, and protein were then combined for each cell as seen in FIG. 9. The cell lines were identified using their SNVs as seen in FIG. 8.

Example II

Figure 10:
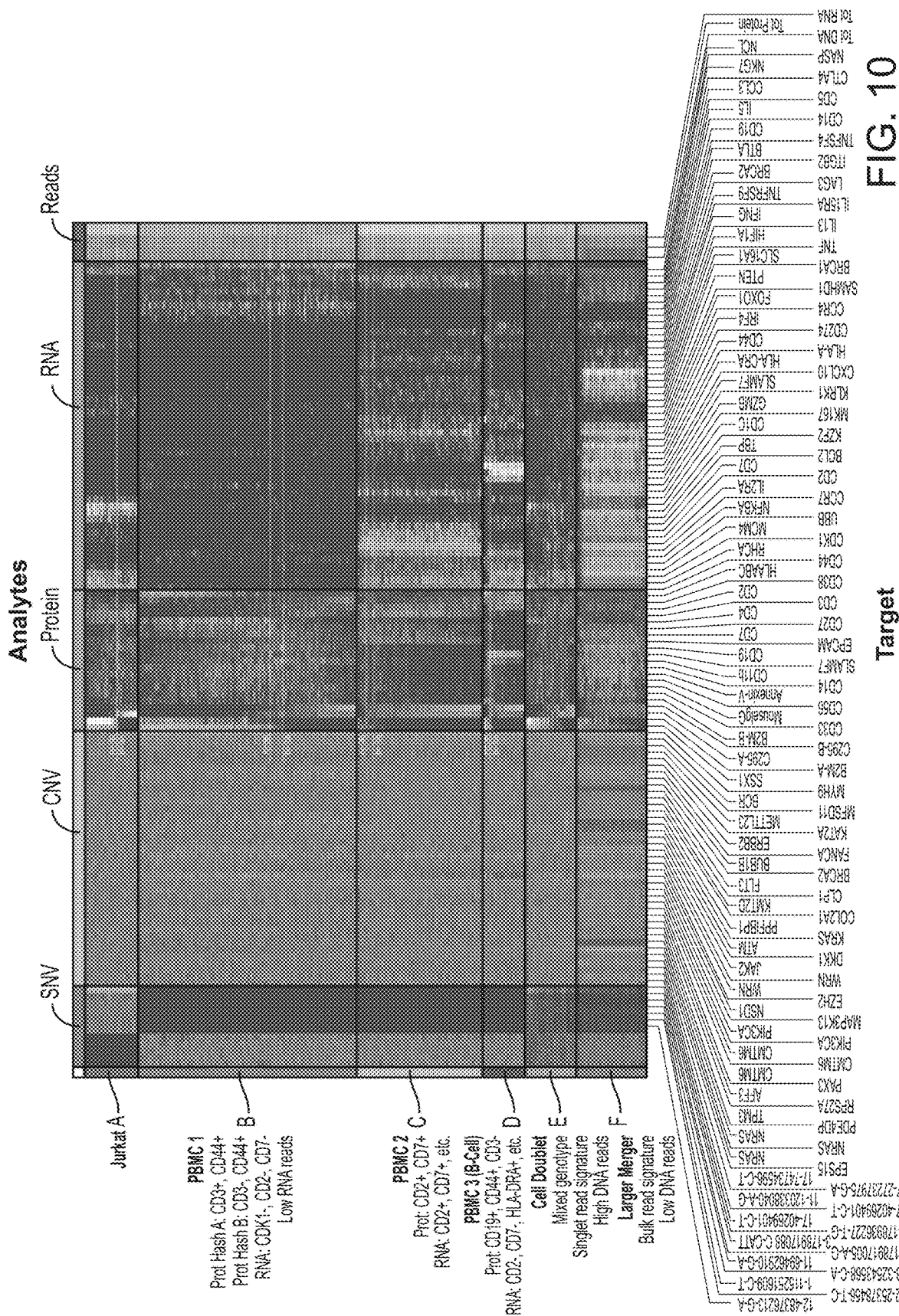
FIG. 10 depicts the results from the multiomics experiment from Example II where PBMCs were untreated or treated with PHA. A spike-in of the Jurkat cell line was also included. DNA libraries, RNA libraries, and protein libraries from single cells were produced where the libraries produced from the same cell shared a cell barcode. By looking at the mutations found in the DNA libraries, Jurkat cells, cell doublets, and merged droplets were identified. Each cell barcode also has corresponding RNA reads and protein reads (top).
Figure 11:
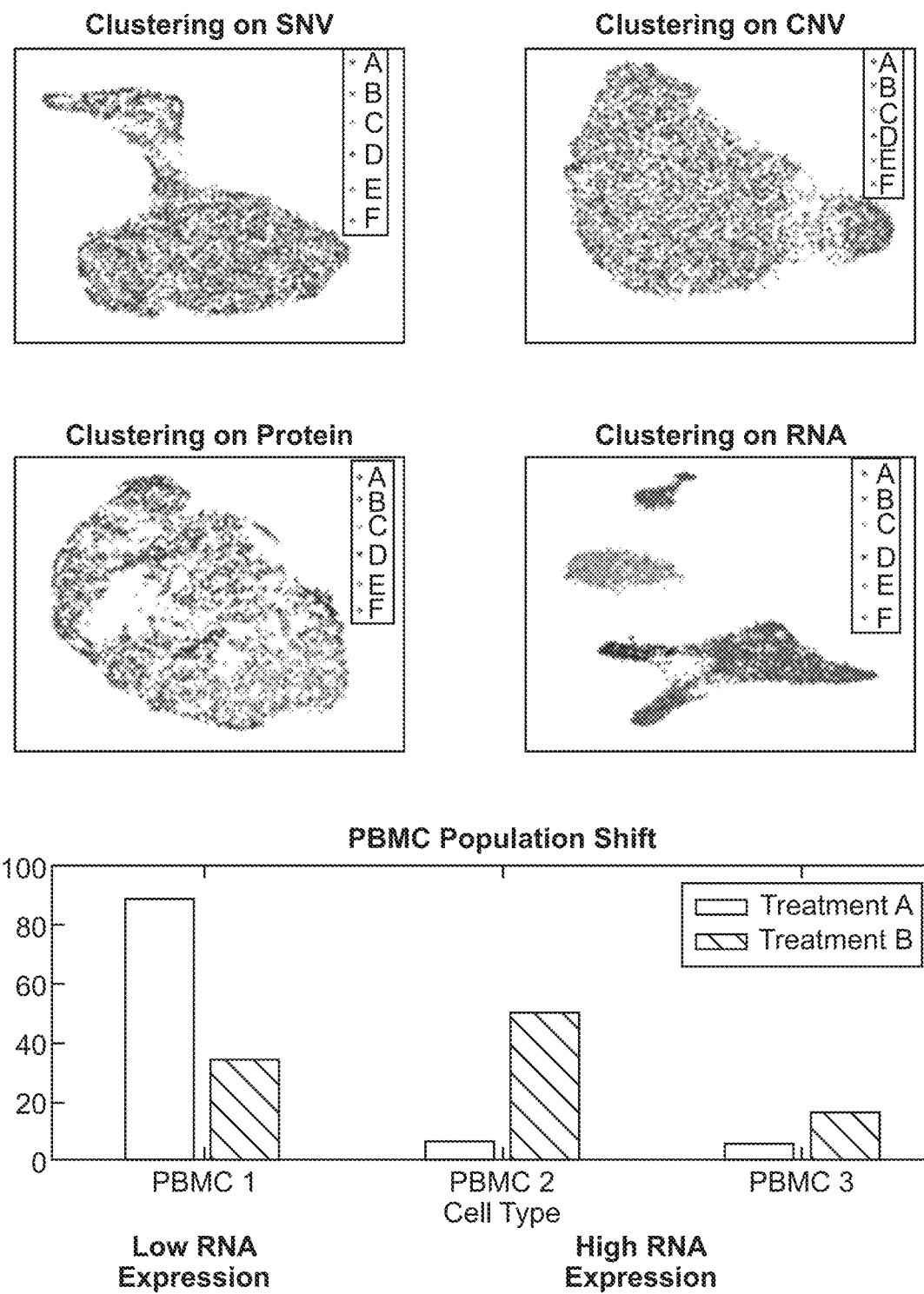
FIG. 11 shows the fraction of PBMCs that had low RNA expression and high RNA expression. The cells were identified as being treated by PHA or untreated by the protein tags used for cell hashing.

In this Example, we provide an embodiment for a single workflow for the simultaneous detection of DNA, RNA, and protein with PBMCs. PBMCs were untreated or treated with PHA. The cells were combined with a small percentage of Jurkat cells then stained with tagged antibodies. These stained cells were then encapsulated on the Tapestri® (a multiomics workflow) instrument with reagents for cell lysis, reverse transcription and protease treatment. Following these reactions, the droplets were then merged with PCR reagents on the Tapestri® (a multiomics workflow) instrument. This reaction attached the cell barcodes onto each amplicon for DNA, RNA, and protein. These amplicons were then used to produce separate sequencing libraries using the workflow described in FIG. 4. Following sequencing, the cell barcodes were used to link the reads from DNA, RNA, and protein to the same cells as seen in FIG. 10. Shown in FIG. 11, these reads could then be used for cluster analysis and expression level analysis.

In an exemplary embodiment, the workflow consists of three discrete processes to access, tag and amplify PCR amplicons for each omic. The general outlay of the exemplary process is summarized below (and reference to FIGS. 1A and 1B):

A bulk suspension of cells (typically from a mammalian source such as a cultured cells, blood-derived and bone marrow-derived cells) are incubated with oligonucleotide-tagged antibodies. The oligonucleotide is attached to the antibody by use of click chemistry. The 5'-end nucleotide sequence comprise a "handle" sequence for hybridization to a "forward" PCR primer. The mid-section of the oligonucleotide contains an antibody-specific barcode and random nucleotide sequence. The 3'-end contains a sequence for the "reverse" PCR primer.

Typically, 0.1-50 nM of oligo-tagged antibody is incubated with 1,000-1,000,000 cells in a volume of 1-1000 uL. After 0.1-20 hours incubation at 4-37 C temperature, the cells are wash with 0.1-100 mL of wash buffer. After 2-8 washes, the cells are resuspended in 10-1000 uL for loading onto a Tapestri® (a multiomics workflow) cartridge.

The single cells are combined into the first droplet merger containing reagents for reverse transcription and a protease lysis buffer. After a brief reverse transcription and protease incubation, the protease is heat inactivated at 70-95 C for 2-60 minutes.

The first droplet is then merged with a second droplet containing the cell barcoded bead, PCR hot start enzyme and complete buffer, multiplex forward and reverse primers for both targeted DNA and RNA. After a 1-60 minute incubation to prime and extend RNA templates, the droplets are heated to 80-95 C 1-30 minutes to activate the thermostable PCR enzyme.

PCR amplification of antibody, RNA/cDNA and DNA targets is commenced by the standard Tapestri® (a multiomics workflow) cycling conditions, with tolerances added.

After the first round of PCR, the emulsion is eliminated and the PCR product aqueous phase carried forward.

A biotin-labeled oligonucleotide directed to hybridize to the antibody reverse primer sequence region and thereby selectively isolates the antibody tags away from the RNA and DNA amplicons.

Both the DNA, RNA and protein amplicon fractions are selectively purified by AMPure bead process (beads and instructions available from Beckman Coulter, Fullerton Calif.).

A second round of PCR with Illumina compatible sequencing primers is commenced on the single-cell libraries. Different sample indexes can be used for each analyte.

The DNA, RNA and Protein libraries are combined together at a range varying from 1:100 to 100:1 ratio, depending on the desired read distribution of DNA to RNA to protein. The mixture is loaded onto an Illumina sequencing platform.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A multiomic detection method for detecting DNA, RNA, and protein from a cell, comprising:
  combining the cell with antibody-oligonucleotide tags, wherein antibodies of the antibody-oligonucleotide tags exhibit specificity for proteins of the cell;
  encapsulating the cell and antibody-oligonucleotide tags in a drop comprising a reaction mixture comprising a protease;
  performing a protease digest on the encapsulated cell drop with the protease to produce a cell lysate, wherein the cell lysate comprises DNA, RNA, and oligonucleotide tags derived from the antibody-oligonucleotide tags;
  providing a reverse transcriptase and generating cDNA by performing a reverse transcription reaction on the RNA;
  combining cell lysate comprising DNA, cDNA, and oligonucleotide tags with barcoding reagents and barcoding beads;
  performing a nucleic acid amplification reaction to attach the cell barcodes to amplicons derived from the DNA, cDNA, and oligonucleotide tags, wherein amplicons from the drop contain a same cell barcode; and
  detecting DNA, RNA, and protein of the cell by sequencing the cell barcode incorporated into the amplicons.

2. A method according to claim 1, wherein the DNA, RNA, and protein of the cell are detected simultaneously.

3. A method according to claim 1, wherein the reverse transcription reaction is performed in the same drop as the protease digest.

4. A method according to claim 1, further comprising performing an exonuclease reaction and a cleanup to separate the amplicons derived from the oligonucleotide tags from the amplicons derived from the DNA and cDNA.

5. A method according to claim 1, wherein the reverse transcriptase reactions are performed on a PCR thermocycler.

6. A method according to claim 1, further comprising making a protein library.

7. A method according to claim 1, further comprising making a DNA library.

8. A method according to claim 1, further comprising making an RNA library.

9. A method according to claim 1, further comprising making DNA, protein, and RNA libraries.

10. The method of claim 1, wherein providing a reverse transcriptase and generating cDNA further comprises using reverse transcriptase enzyme with RNA-specific primers to extend RNA and generate cDNA templates for detecting the RNA.

11. The method of claim 1, wherein the multiomic detection comprises a triomic interrogation process for the cell.

12. The method of claim 1, wherein the nucleic acid amplification reaction is used to amplify the DNA, cDNA, and antibody-oligonucleotide tags.

13. The method of claim 9, further comprising determining an identity of an analyte by purifying and quantifying the DNA, protein, and RNA libraries.

14. The method of claim 13, wherein the amplicons are selectively purified by a bead purification process.

15. The method of claim 4, wherein performing an exonuclease reaction and a cleanup generates supernatant for processing into protein libraries.

16. The method of claim 4, wherein performing an exonuclease reaction and a cleanup generates beads comprising the amplicons derived from DNA and cDNA.

17. The method of claim 16, further comprising separating the amplicons derived from DNA and cDNA using a biotin capture oligo and streptavidin beads.

18. The method of claim 1, wherein the barcoding reagents are barcoding PCR reagents.

* * * * *